(12) United States Patent
Amirkhanian et al.

(10) Patent No.: US 7,622,083 B2
(45) Date of Patent: Nov. 24, 2009

(54) MULTI-CAPILLARY ELECTROPHORESIS CARTRIDGE INTERFACE MECHANISM

(75) Inventors: Varouj Amirkhanian, La Crescenta, CA (US); Bob G. Heitel, Laguna Beach, CA (US); Ming-Sun Liu, Brea, CA (US); Paul Mooney, Rancho Santa Margarita, CA (US)

(73) Assignee: Biocal Technology, Inc., Irvine, CA (US)

( * ) Notice: Subject to any disclaimer, the term of this patent is extended or adjusted under 35 U.S.C. 154(b) by 888 days.

(21) Appl. No.: 10/823,382

(22) Filed: Apr. 12, 2004

(65) Prior Publication Data

US 2005/0016852 A1 Jan. 27, 2005

Related U.S. Application Data

(63) Continuation-in-part of application No. 10/059,993, filed on Jan. 28, 2002, now Pat. No. 7,309,409, and a continuation-in-part of application No. 10/060,052, filed on Jan. 28, 2002, now Pat. No. 6,828,567, and a continuation-in-part of application No. 10/319,803, filed on Dec. 13, 2002, now Pat. No. 7,250,099, and a continuation-in-part of application No. PCT/US03/39971, filed on Dec. 15, 2003.

(60) Provisional application No. 60/462,481, filed on Apr. 11, 2003.

(51) Int. Cl.
*B01L 11/00* (2006.01)
(52) U.S. Cl. ..................................... 422/103
(58) Field of Classification Search .................. 422/103
See application file for complete search history.

(56) References Cited

U.S. PATENT DOCUMENTS 5,415,841 A * 5/1995 Dovichi et al. ............. 422/68.1
2002/0092770 A1 7/2002 Hedberg et al.

FOREIGN PATENT DOCUMENTS

EP 0021499 1/1981

(Continued)

OTHER PUBLICATIONS

Partial International Search Report of Counterpart PCT Application No. PCT/US2004/043424.

(Continued)

*Primary Examiner*—Walter D Griffin
*Assistant Examiner*—Bobby Ramdhanie
(74) *Attorney, Agent, or Firm*—Liu & Liu

(57) ABSTRACT

The present invention provides for an interface mechanism in a bio-separation instrument that makes interface connections to a multi-channel cartridge. The interface mechanism precisely positions the cartridge in relation to the support elements in the instrument (e.g., high-voltage, gas pressure, incident radiation and detector), and makes automated, reliable and secured alignments and connections between various components in the cartridge and the support elements in the supporting instrument. The interface mechanism comprises pneumatically or electromechanically driven actuators for engaging support elements in the instrument to components on the cartridge. After the cartridge has been securely received by the interface mechanism, the connection sequence is initiated. The interface provides separate high voltage and optical connections for each separation channel in the cartridge, thus providing channel-to-channel isolation from cross talk both electrically and optically.

18 Claims, 34 Drawing Sheets

FOREIGN PATENT DOCUMENTS

| | | |
|---|---|---|
| EP | 0631134 | 7/2002 |
| JP | 11023533 | 1/1999 |
| JP | 11230938 | 8/1999 |
| WO | WO 02/28509 | 4/2002 |
| WO | WO 02/059589 | 8/2002 |

OTHER PUBLICATIONS

International Search Report of Counterpart PCT Application No. PCT/US2004/011376.

\* cited by examiner

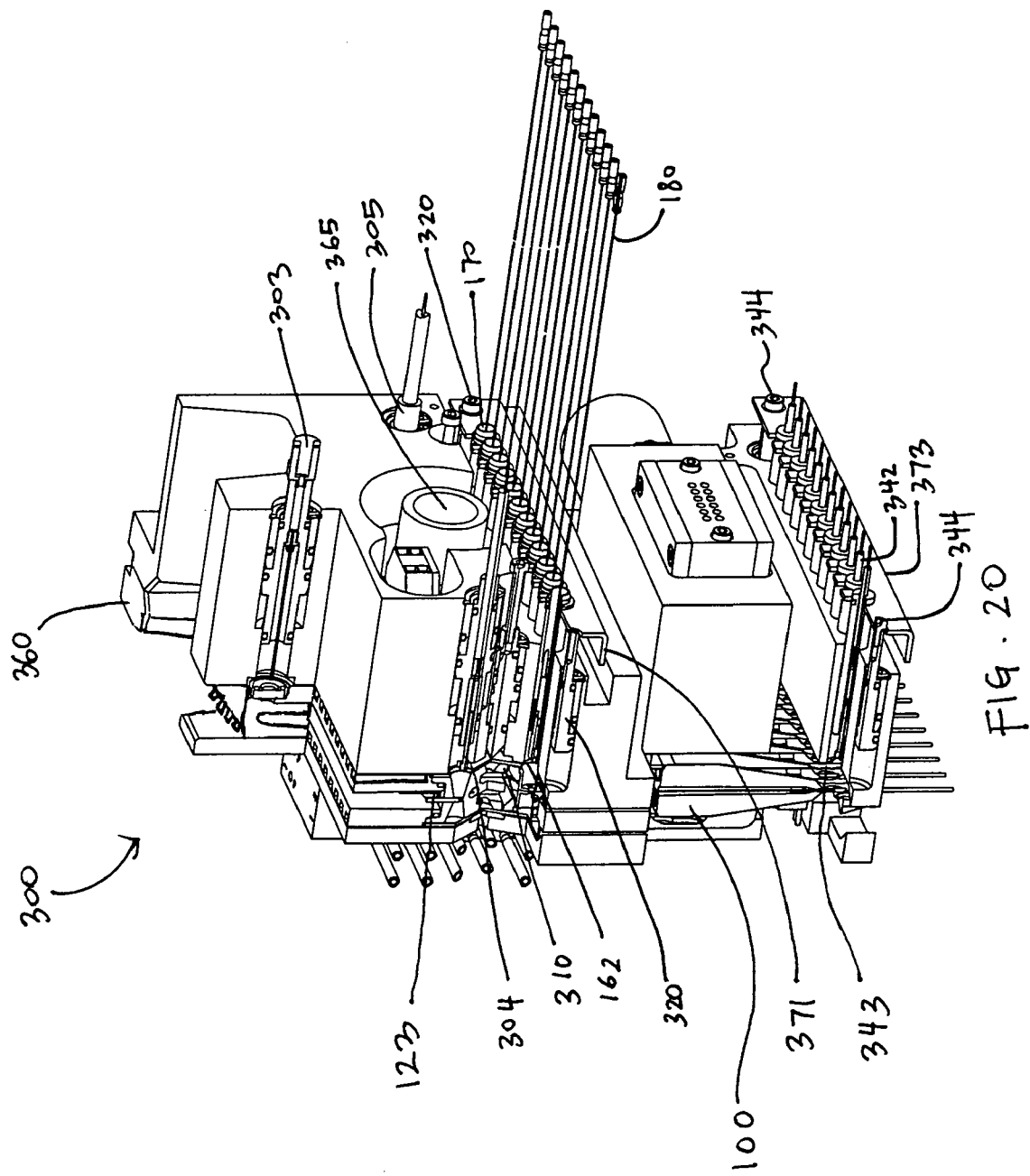

MULTI-CAPILLARY ELECTROPHORESIS CARTRIDGE INTERFACE MECHANISM

This application claims the priority of U.S. Provisional Patent Application No. 60/462,481, filed on Apr. 11, 2003.

This application is a Continuation-in-Part of U.S. patent application Ser. No. 10/059,993 entitled "Multi-Channel Bio-Separation Cartridge," filed on Jan. 28, 2002 now U.S. Pat. No. 7,309,409; and U.S. patent application Ser. No. 10/060,052, entitled "Optical Detection In A Multi-Channel Bio-Separation System", filed on Jan. 28, 2002 now U.S. Pat. No. 6,828,567; and U.S. patent application Ser. No. 10/319,803, entitled "Optical Detection Alignment Coupling Apparatus", filed on Dec. 13, 2002 now U.S. Pat. No. 7,250,099; and PCT Application No. PCT/US03/39971, entitled "Optical Detection Alignment Coupling Apparatus", filed on Dec. 15, 2003; which are commonly assigned to BioCal Technology, Inc., the assignee of the present invention.

The above-mentioned applications, and all other applications, documents and references noted in the disclosure herein below, are fully incorporated by reference as if fully set forth herein.

BACKGROUND OF THE INVENTION

The present invention relates to bio-separation, and more particularly to an interface mechanism in a bio-separation instrument, which supports the use and functions of a multi-channel capillary cartridge, in particular a multi-channel cartridge having multi-separation columns with integrated reagent reservoir and excitation radiation and detection optics.

Bioanalysis, such as DNA analysis, is rapidly making the transition from a purely scientific quest for accuracy to a routine procedure with increased, proven dependability. Medical researchers, pharmacologists, and forensic investigators all use DNA analysis in the pursuit of their tasks. Yet due to the complexity of the equipment that detects and measures DNA samples and the difficulty in preparing the samples, the existing DNA analysis procedures are often time-consuming and expensive. It is therefore desirable to reduce the size, number of parts, and cost of equipment, to ease sample handling during the process, and in general, to have a simplified, low cost, high sensitivity detector.

One type of DNA analysis instrument separates DNA molecules by relying on electrophoresis. Electrophoresis techniques could be used to separate fragments of DNA for genotyping applications, including human identity testing, expression analysis, pathogen detection, mutation detection, and pharmacogenetics studies. The term electrophoresis refers to the movement of a charged molecule under the influence of an electric field. Electrophoresis can be used to separate molecules that have equivalent charge-to-mass ratios but different masses. DNA fragments are one example of such molecules.

There are a variety of commercially available instruments applying electrophoresis to analyze DNA samples. One such type is a capillary electrophoresis (CE) instrument. By applying electrophoresis in a fused silica capillary column carrying a buffer solution, the sample size requirement is significantly smaller and the speed of separation and resolution can be increased multiple times compared to the slab gel-electrophoresis method. These DNA fragments in CE are often detected by directing light through the capillary wall, at the components separating from the sample that has been tagged with a fluorescence material, and detecting the fluorescence emissions induced by the incident light. The intensities of the emission are representative of the concentration, amount and/or size of the components of the sample. In the past, Laser-induced fluorescence (LIF) detection methods had been developed for CE instruments. Fluorescence detection is often the detection method of choice in the fields of genomics and proteomics because of its outstanding sensitivity compared to other detection methods.

Some of the challenges in designing CE-based instruments relate to the support of the capillaries and alignment of the capillaries to support elements (e.g., excitation and detection optics). Biocal Technology, Inc. developed a CE-based instrument and a multi-channel cartridge for use therein, which comprises multi-separation columns with integrated reagent reservoir and excitation radiation and detection optics. (The Biocal cartridge and system are described in U.S. patent application Ser. No. 10/059,993 and U.S. patent application Ser. No. 10/060,052, which had been incorporated by reference herein). The cartridge is designed to be supported by the instrument, with all essential cartridge elements aligned and coupled to support elements in the instrument. It is desirable to provide a reliable and secure interfacing mechanism in the instrument to make such coupling to the cartridge.

SUMMARY OF THE INVENTION

The present invention provides for an interface mechanism in a bio-separation instrument that makes interface connections to a multi-channel cartridge. One aspect of the present invention provides an interface mechanism that precisely positions the cartridge in relation to the support elements (e.g., electrical power such as high-voltage, gas pressure, incident radiation and detection optics) provided by the supporting instrument, and makes automated, reliable and secured alignments and connections between various components in the cartridge and the support elements in the instrument. Such alignments and connections are reliably implemented, in a reliable automated sequence, after the cartridge had been securely received by the interface mechanism.

In another aspect of the present invention, the interface mechanism comprises pneumatically or electro-mechanically driven actuators for engaging structures on the cartridge, to securely connect at least one of gas pressure, high voltage, emission detection optics, and excitation radiation optics. In one embodiment, the pneumatically driven actuators comprise gas driven pistons. After the cartridge has been securely received by the interface mechanism, the connection sequence is initiated. In one embodiment, the connection sequence is initiated by a user. Alternatively, the connection sequence may be initiated automatically in response to a secured reception of the cartridge to the interface mechanism. A disconnection sequence is provided to disconnect the support elements from the cartridge, allowing the cartridge to be safely removed from the instrument.

In a further aspect of the present invention, the interface provides separate high voltage and optical connections for each separation channel in the cartridge, thus providing channel-to-channel isolation from cross talk both electrically and optically.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the follow

FIGS. 20 and 21 is a rear perspective view of the interface mechanism in accordance with one embodiment of the present invention.

DETAILED DESCRIPTION OF ILLUSTRATED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides for an interface mechanism bio-separation instrument that supports a multi-segment cartridge. For purpose of illustrating the principles of the present invention and not by limitation, the present invention is described by reference to embodiments directed to capillary electrophoresis and radiation induced fluorescence.

Overview of CE

Figure 1:
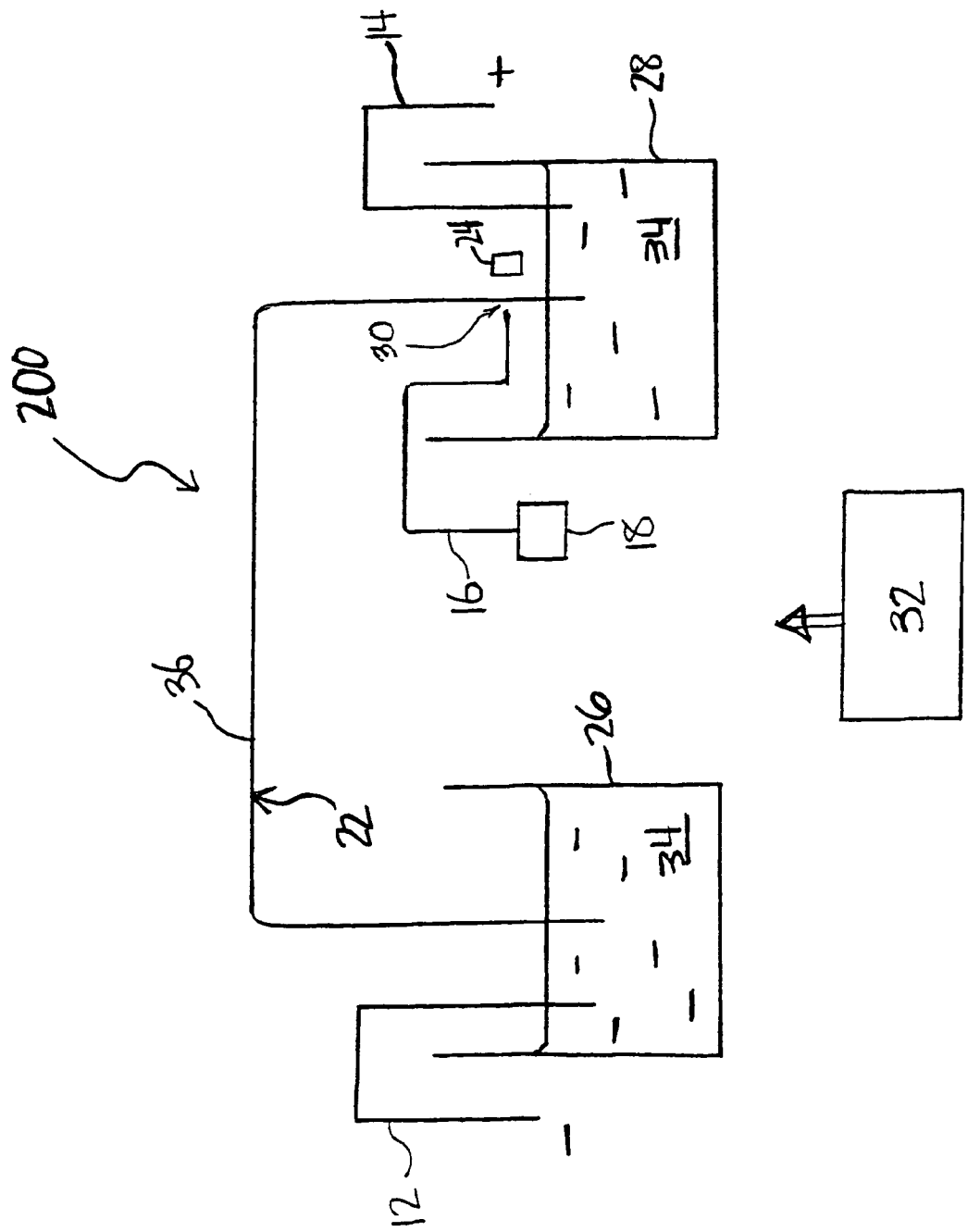
- FIG. 1 is a schematic view of a capillary electrophoresis system that incorporates the present invention.

Referring to FIG. 1, a bio-separation system, more specifically a capillary electrophoresis (CE) system 200 that incorporates the present invention is schematically illustrated. The CE system 200 generally comprises a capillary separation column 22 (e.g., 200-500 µm O.D.), which defines a separation channel 36 (e.g., 25-200 µm I.D.). The capillary column 22 may be made of fused silica, glass, polyimide, or other plastic/ceramic/glassy materials. The inside walls of the separation column 22 (i.e., the walls of the separation channel 36) may be coated with a material that can build up an electrostatic charge to facilitate electrophoresis and/or electrokinetic migration of the sample components. The separation channel 36 is filled with a separation support medium, which may simply be a running buffer, or a sieving gel matrix known in the art. For radiation induced fluorescence detection, the gel matrix includes a known fluorophore, such as Ethidium Bromide.

One end of the capillary column 22 is submerged in a reservoir 28 of running buffer/gel 34. The other end of the capillary column 22 is coupled to the sample vial 26. It is understood that the detection configurations shown in the other embodiments can be equally implemented in a system similar to the CE system 20. Also, the separation channel 36 may be one straight capillary or micro-channel with a section of the detection window closest to the gel-reservoir at the exit end being the detection zone, which is the current preferred mode of our invention. A radiation detector 24 is positioned outside a transparent section of the capillary walls at detection zone 30. An excitation fiber 16 extends from a radiation source 18 (e.g., LED or laser) and is directed at the detection zone 30 outside the walls of the column. Electrodes 12 and 14, that are part of the cartridge assembly are coupled to the buffer reservoirs 26 and gel reservoir 28 to complete the electrophoresis path.

For the sake of completeness, it is sufficient to briefly mention the operation of the CE system 200. In operation, a prepared biological sample (e.g., a DNA sample), direct from Polymerase Chain Reaction (PCR) machine is introduced into the far end of the capillary column away from the detection zone by any of a number of ways that is not part of the present invention (e.g., electrokinetic injection from a sample reservoir or physical pressure injection using a syringe pump). The sample binds to the fluorophore.

When a DC potential (e.g., 1-30 KV) is applied between electrodes 12 and 14, the sample migrates under the applied electric potential along the separation channel 36 (e.g. DNA that is negatively charged travels through the sieving gel with an integrated dye matrix/fluorophore toward a positive electrode as shown in FIG. 1) and separates into bands of sample components. The extent of separation and distance moved along the separation channel 36 depends on a number of factors, such as migration mobility of the sample components, the mass and size or length of the sample components, and the separation support medium. The driving forces in the separation channel 36 for the separation of samples could be electrophoretic, pressure, or electro-osmotic flow (EOF) means.

When the sample reaches the detection zone, excitation radiation is directed via the excitation fiber 16 at the detection zone. The sample components fluoresce with intensities proportional to the concentrations of the respective sample components (proportional to the amount of fluorescent tag material). The detector 24 detects the intensities of the emitted fluorescence at a wavelength different from that of the incident radiation. The detected emitted radiation may be analyzed by known methods. For an automated system, a controller 32 controls the operations of the CE system 200.

Multiple Capillary Cartridge Based CE System

Figure 2:
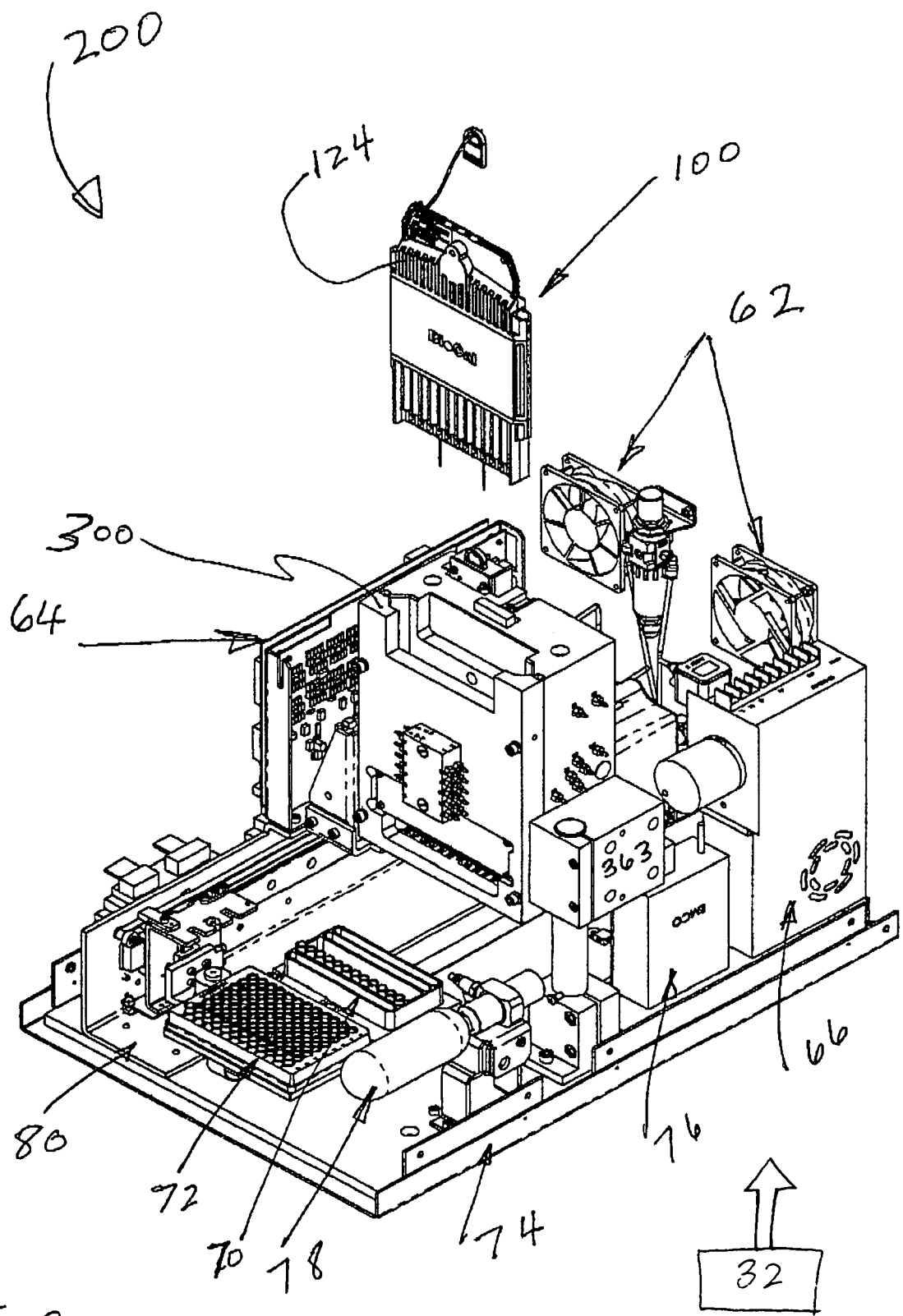
FIG. 2 is a perspective view of the capillary electrophoresis system/machine in accordance with one embodiment of the present invention.

FIG. 2 shows an overall perspective view of the CE system 200 (e.g., an DNA Analyzer). The CE system 200 incorporates an interface mechanism 300 (only rear support block 363 is shown in FIG. 2, otherwise schematically and generally represented as a dotted line structure in FIG. 2 to not obscure the cartridge 100), in accordance with one embodiment of the present invention. The interface mechanism 300 supports a multi-channel cartridge 100 in accordance with the one embodiment of the present invention, which provides easy handling of multi-channel separation columns, and allows easy optical coupling of the detection zones to the detection optics of the CE system 200. Details of the interface mechanism 300 will be described below. The fully automated DNA analysis system 200 has a base 74, supporting a modular X-Z sample handling tray mechanism 80, which moves one 96-well micro-titer plates 70 and a buffer plate 72 in relation to the multi-capillary cartridge 100 supported by the interface mechanism 300. The system 200 provides easy handling of multi-channel separation columns, and allows easy optical coupling of the detection zones to the detection optics of the CE system 200. The operations of the CE system 200, including the interface mechanism 300, is controlled by a controller 32.

Figure 3:
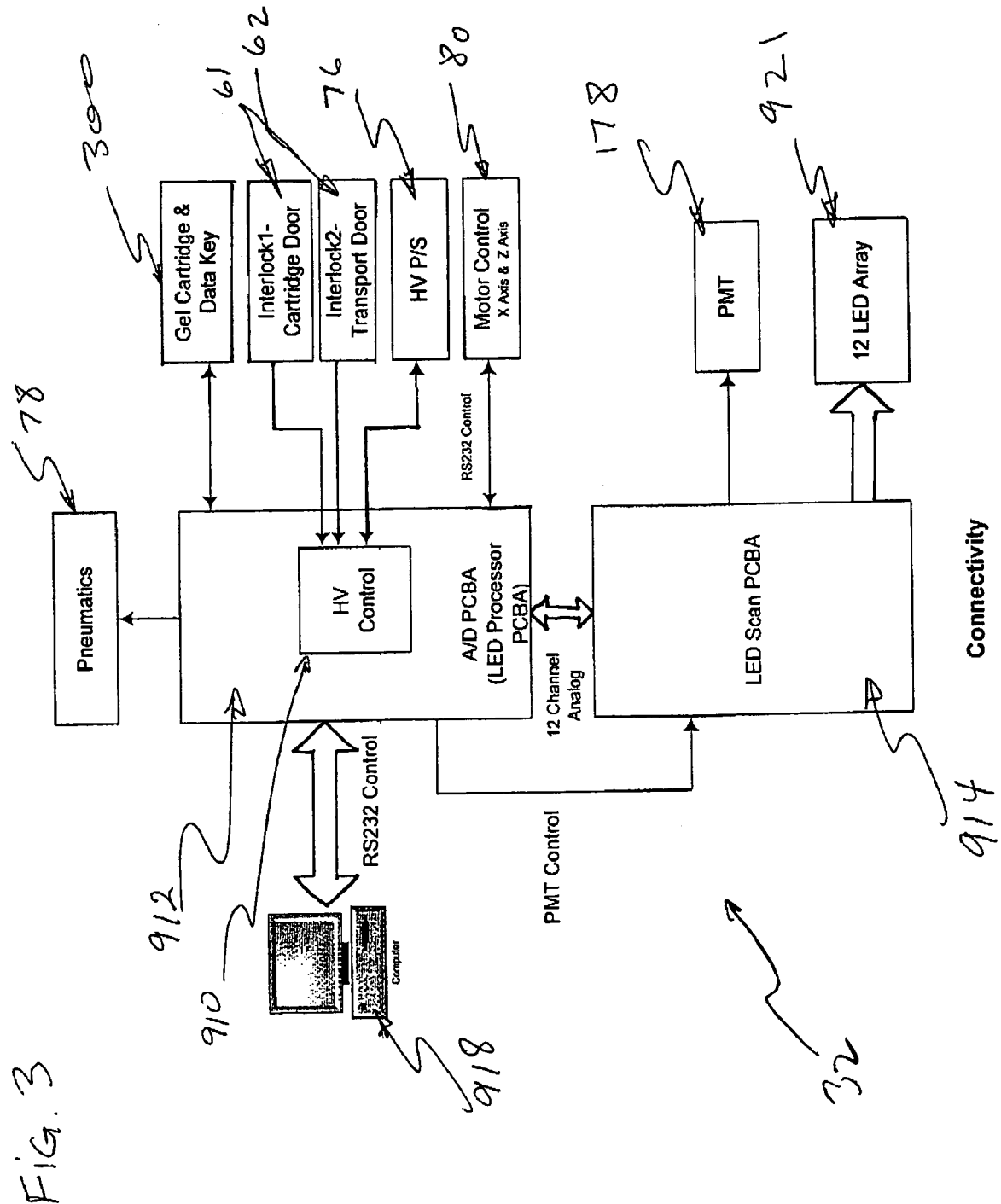
FIG. 3 is a diagram of the control system.

In accordance with one embodiment of the present invention, the block diagram of the controller 32 for the CE system 200 is shown in FIG. 3. The controller comprises a processor as part of the A/D Board (LED Processor) 912 with CPU 910 for converting detection signals received from the PMT 178 (FIG. 13) to corresponding digital signals, coming from LEDScan PCBA interface 914 for transferring and receiving signals to and from respective parts of the CE system 200 by instructions from the CPU 910. The A/D (LED Processor PCBA) interface 912 is coupled to the various actuators in the interface mechanism 300 to control and connect (using the interface mechanism 300) at least high voltage power supply 76, pneumatics 78, motor controls (X-Z sample/buffer tray) 80 and interlocks (cartridge and transport doors) 61 and 62. The A/D or LED Processor PCBA 912 also controls the high-voltage power supply 76 for sample injection and electrophoresis functions of the CE system 200, a circuit 914 (LEDScan Board) for modulating the excitation radiation source (e.g., LEDs) 921 and the PMT detector module 178, of the CE system 200. The A/D (LED Processor PCBA) 912 may be further coupled to an external personal computer 918, which in turn performs data processing or additional control function for the CE system 200 using BioCal's BioCalculator Software to control various features and functions of the automated multi-channel DNA analyzer 200.

The components of the controller 32, with the exception of the PC 218, may be packaged as an electronic board 64 (FIG. 2) and cooling fans 62, on board the CE system 200 and electrically coupled to the PC 218 via a serial port (not shown), or they may be part of a separate controller module outside of the CE system 200. The CPU 210 and/or the PC 218 are programmed to accomplish the various control functions and features for the CE system 200. In one embodiment, the PC 218 can be configured to provide the user control interface for the CE system 200 (e.g., user initiation of the connection sequence of the interface mechanism 300). It would be within a person skilled in the art to implement the program code given the functions and features disclosed herein. In an alternate embodiment, the controller 32 or components thereof may be incorporated as part of the PC 218.

Capillary Cartridge

The multi-channel capillary cartridge 200 includes twelve detection zones 155 (See FIG. 8, which is also schematically represented as 30 in FIG. 1), defined by capillaries 140 held in a cartridge body. The cartridge 100 includes a twelve-channel fused silica capillary array that is used for separation and detection of the samples as part of a disposable and/or portable, interchangeable cartridge assembly 100. The cartridge 100 shown in FIG. 2 holds up to 12 capillaries 140, 12-18 cm long. The cartridge 100 is integrated with a top, outlet buffer reservoir 130 common to all capillaries 140, which is directly coupled by the interface mechanism 300 to a modular compressed gas source 78, such as a replaceable pressurized gas cartridge of an inert, compatible or non-reactive gas (e.g., Nitrogen, $CO_2$, etc.) or a pressure pump. Appropriate pressure plumbing, including tubing, pressure valve and solenoid controls, is provided. (Details of such plumbing are omitted, since it is well within one skilled in the art to configure such plumbing given the disclosure herein of the functions, features and operations of the system 200.) The pressure source 78 provides the required gas pressure to fill-up all the 12-capillaries with the sieving gel contained in the reservoir 130 and to purge the gel from the previous run from the capillaries during the refilling process. Depending on the viscosity of the gel, pressures of up to 40 PSI may be applied to the capillaries 140 through the gel-filled reservoir 130. The cartridge gel-reservoir 130 is equipped with a built in common electrode anode 134 (see FIGS. 7 and 8) for all 12-capillaries, which is automatically connected by the interface mechanism 300 to a high voltage power supply 76 (FIG. 2) for electrophoresis when installed inside the system 200. A fan or Peltier cooler on the adjacent structure to the cartridge 100 provides temperature control of the cartridge. The cartridge will have vent holes (input and output) for air circulation (temperature controlled air to be introduced to the cartridge from the instrument side). A power supply 66 (FIG. 2) provides DC power to the CE system 200.

Figure 4:
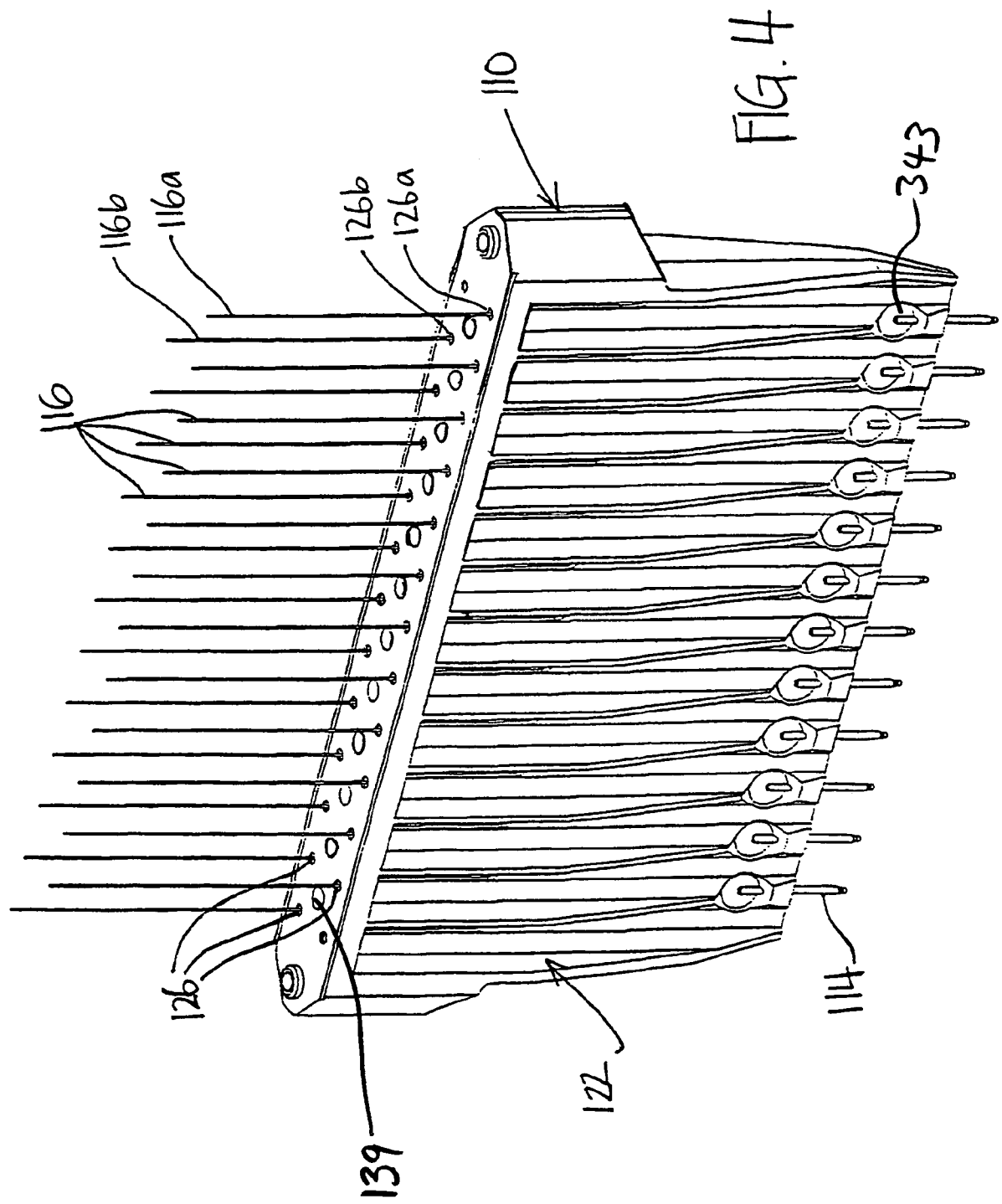
FIG. 4 is a perspective view of the cartridge lower section with excitation fibers.

FIGS. 4-16 illustrate in detail the assembly of the components for the cartridge (the covers 146 and 148 at the mid-section 120 is omitted from view, to show the internal components). They are described here for illustrative purposes and are not to be taken in a limiting sense. FIG. 4 shows the lower-section body 110 of the cartridge 100. At the upper end of the lower-section body 110 are openings 126 through which portions of the excitation fibers 116 are placed; after being placed through these openings, the excitation fibers 116 are bonded in place. (Other means of securing these components may be used as well.) At the lower end of the lower-section body 110 are cathode electrodes 114 that are also bonded to the lower section 110 (or insert molded as part of the lower section 110). The capillaries 140 (FIG. 7) are inserted through holes 137 and guided to these cathode electrodes 114. Ports 343 provides external access to the cathodes 114 by cathode contacts 342 described in connection with the interface mechanism 300 below. For a twelve-capillary cartridge, there are twice as many excitation fibers (i.e., twenty-four excitation fibers), in case of upgrading for dual-wavelength type detections. These excitation fibers 116 are positioned to alternate around the twelve capillaries 140. This is seen more clearly as fiber openings 126*a* and 126*b* may be used for excitation fibers 1116*a* and 116*b* (FIG. 4) for capillary 140, respectively.

Figure 5:
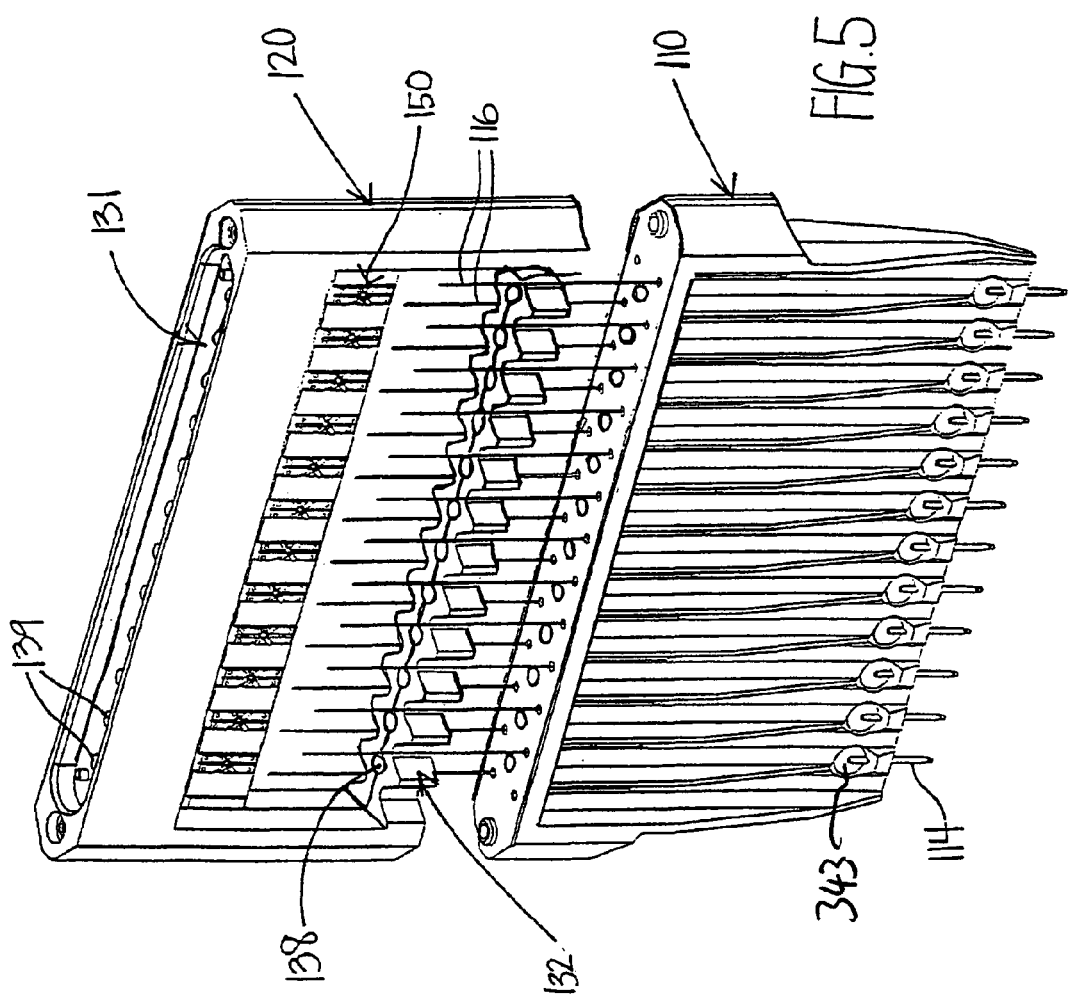
FIG. 5 is a perspective view of the cartridge mid-section and the lower section with excitation fibers before being joined.

FIG. 5 shows the addition of the cartridge mid-section body 120 to the lower-section body 110 in FIG. 4. The cartridge mid-section body 120 is designed so that the part 132 does not obstruct the path of the excitation fibers 116 or that of the capillaries 140. The part 132 has cutouts that provide clearance to or do not enclose the excitation fibers 116. This part 132 also has holes 138 through which the capillaries 140 are placed, as will be shown in further figures. The top end 131 of the mid-section body 120, which will form part of the reservoir, also has holes 139 through which the capillaries 140 will be placed.

Figure 6:
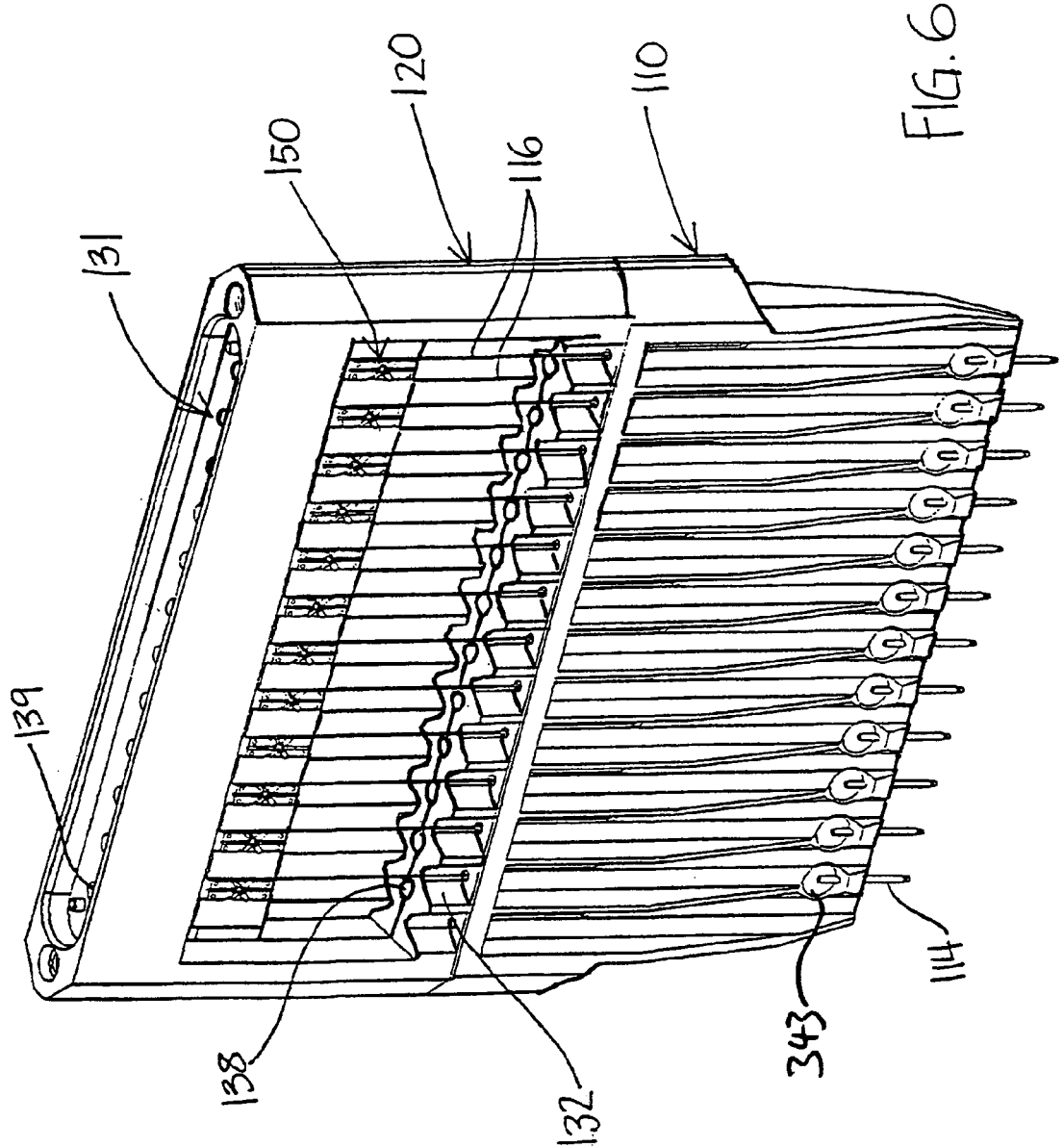
FIG. 6 is a perspective view of the cartridge mid-section and the lower section with excitation fibers after being joined.
Figure 7:
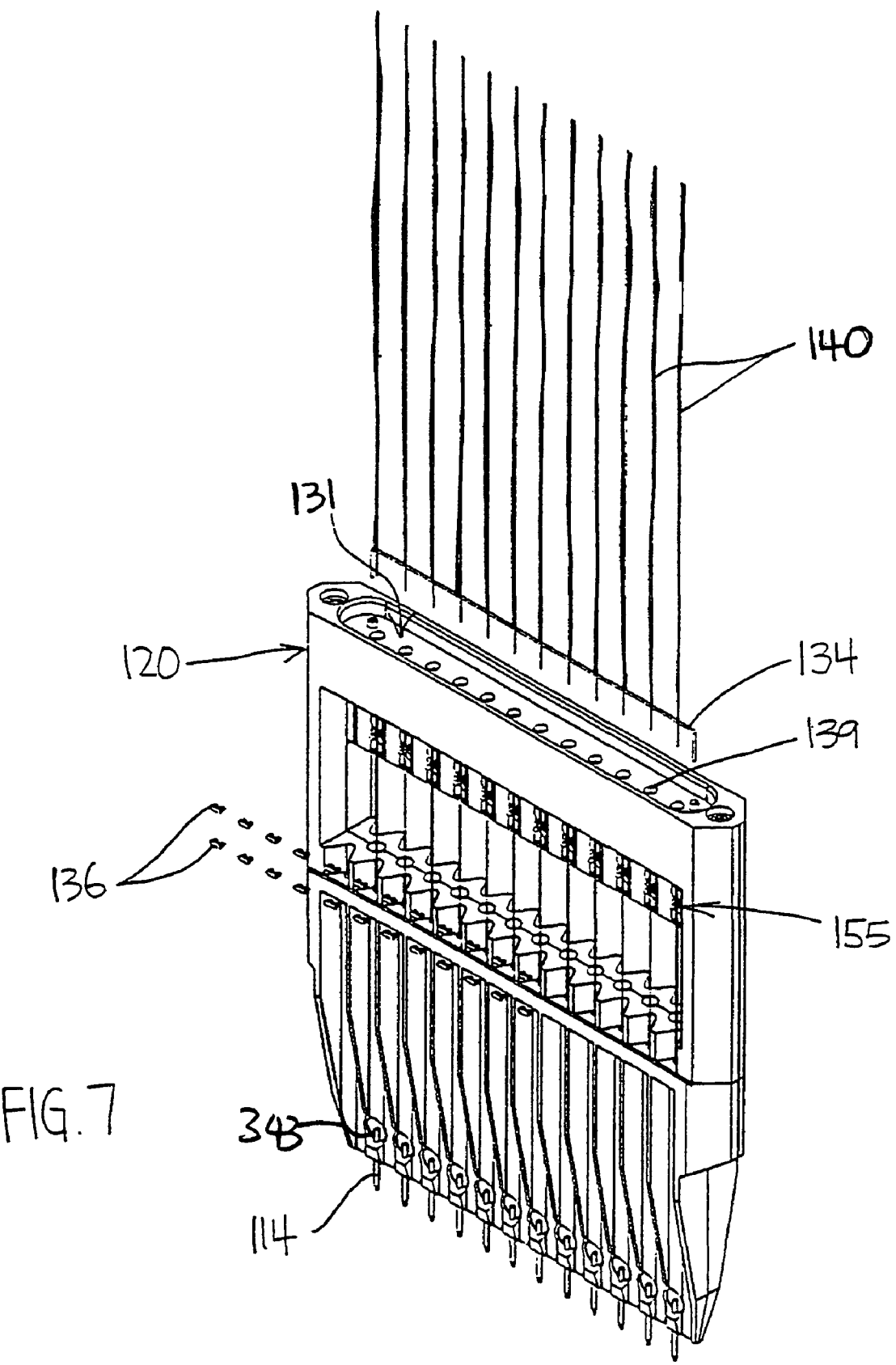
FIG. 7 is a perspective front view of the combined cartridge mid-section and the lower section in FIG. 6 with capillaries before being joined.

After the mid-section body 120 of the cartridge is mounted onto the lower-section body 110, as shown in FIG. 6, polyimide coated capillaries 140 are placed through the capillary holes 137, 138 and 139 until they reach the lower end of the lower-section body 110 (see FIG. 7). The capillaries 140 have a pre-burned window, with the polyimide coating removed to provide a detection window. Staples 136 may be used to secure the capillaries 140 to the mid-section body 120 of the cartridge. (Other means of securing these components such as o-rings may be used as well.) At the top end 131 of the mid-section body 120 is a common anode electrode 134 for the capillaries that extends into the reservoir.

Figure 8:
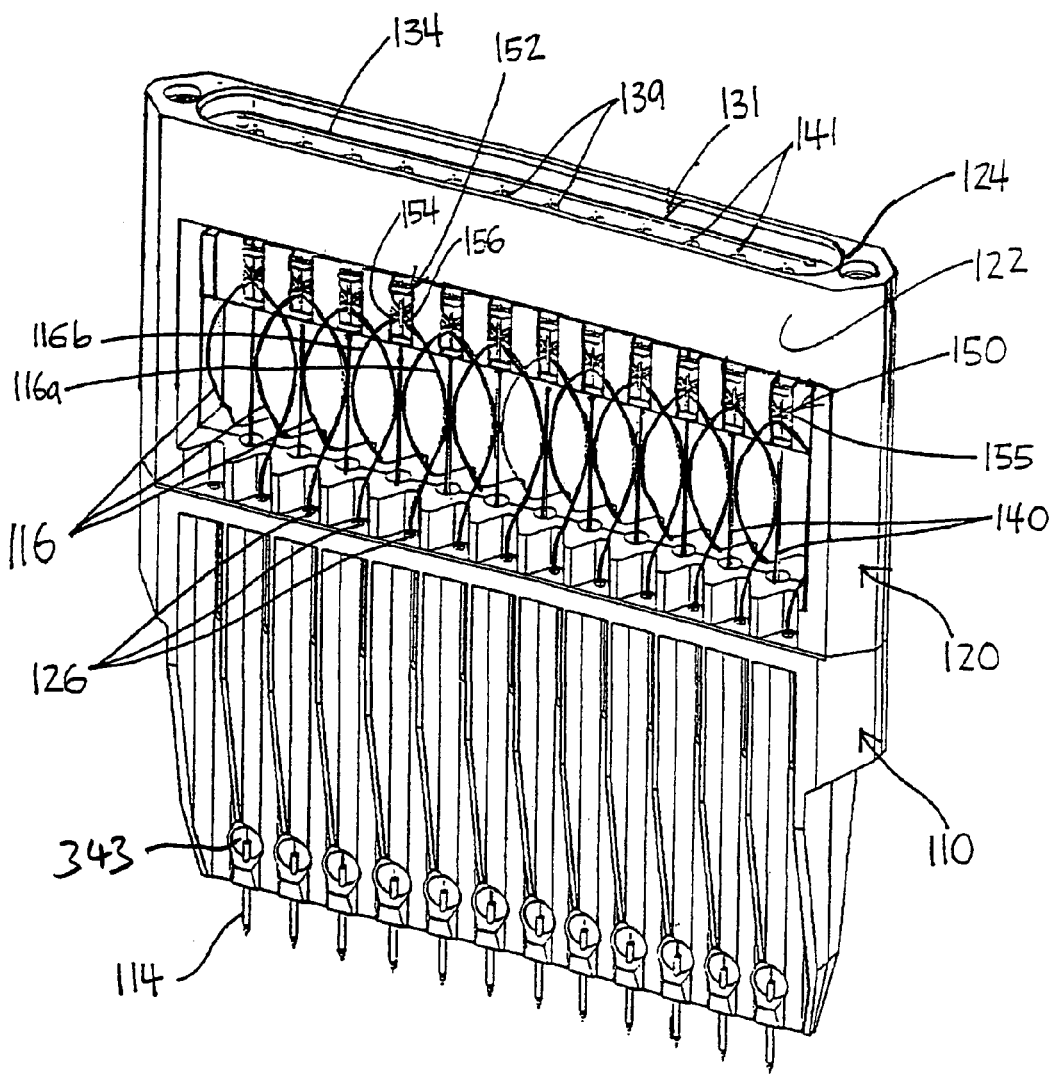
FIG. 8 is perspective front view of the cartridge mid-section and lower section with capillaries after being joined.

FIG. 8 shows the cartridge with the combined mid-section and lower-section bodies 110 and 120, respectively. The capillaries extend from the top of the mid-section body 120 (with the capillary tips 141 protruding at the opening 131 for the reservoir) to the bottom of the lower-section body 110 with the cathodes 114. The detection zone 155 of the capillaries is also shown. The excitation fibers 116 are shown through fiber openings 126 (see also FIG. 4) up to the V-groove block assembly 150, where light from the excitation fibers is directed at the capillaries.

Figure 9:
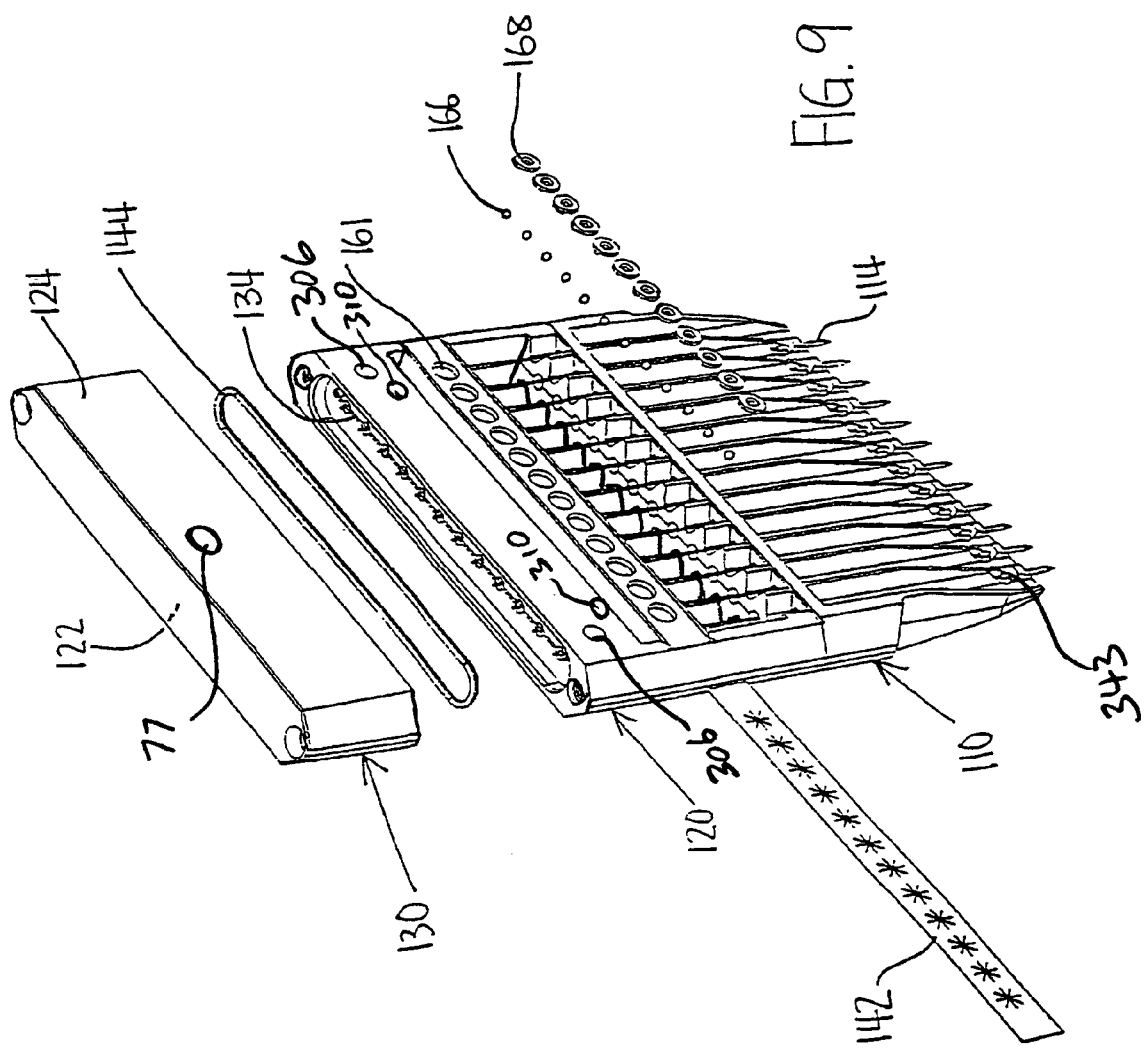
FIG. 9 is a perspective rear view of the cartridge mid-section and lower section with the gel reservoir.

In FIG. 9, a rear view of the cartridge is shown. The cartridge is integrated with a top/outlet buffer reservoir 130 common to all capillaries. The gel reservoir 130 is attached to the mid-section body 120 with an O-ring 144 as a seal. The gel reservoir 130 has a capacity of about 18 cc and may have transparent, or clear, windows on each side for inspection of the gel level. The cartridge 100 has a single common anode 134 at the top opening of the mid-section body 120 and multiple cathodes 114 at the lower-section body 110 as part of the cartridge assembly. (Other means of having two separate electrodes may be used as well.) The cartridge gel reservoir 140 is equipped with a built-in anode 134 common for all twelve capillaries, which is automatically connected to the high voltage power supply 76 via anode contact pins 304 provided on the interface mechanism in the interface module 300, for electrophoresis when installed inside the CE system 200, as will be described below. A commercially available high voltage power supply (i.e. Emco) is used to deliver 0 to 20 KV of electrical field to gel-filled capillaries 140 for the electrokinetic injection and separations of DNA fragments.

The reservoir 130 containing the gel is sealed, such as hermetically sealed at the body of the cartridge, which allows the cartridge to be handled by holding it in an orientation without leakage of the gel. (There is negligible leakage or exposure at the capillary tips because of surface tension and high viscosity within the microbore of the capillaries.) The cartridge 100 has a purge hole 77 that is coupled to purge-air barrel 303 from the instrument (see FIG. 18) that provides compressed gas from the pressure source 78 into the cartridge reservoir 130. This allows pressurized gas to fill the capillaries with the gel/buffer solution before each separation run, and to purge the old gel from the previous run in the process. This approach assures the proper containment of the gel inside the cartridge reservoir; it also provides a simple and reliable means of accessing the gel reservoir and of providing enough gas pressure for the gel to fill up the capillaries prior to applying high voltage to effect CE separation. Depending on the viscosity of the gel, pressures of up to 40 PSI have been applied to the capillaries through the gel-filled reservoir. As will be described below, the interface of the gas pressure to the reservoir 130 is provided by the interface mechanism 300, via the pressure port (hole) 77 provided on the reservoir 130.

The cartridge 100 also has detection optic ports 161 through which detector probes 170 (FIG. 11) are fitted. Through each of these detection optic ports 161, micro-lenses 166 for emission collection optics are placed, followed by elastomer lens retainers 168. The cartridge also has a shutter covering, or a multi-channel aperture strip 142, at the detection optic port 161. The aperture strip 142 may be a thin Polyester material about 0.5 mm thick, which will prevent any dust particles or foreign objects from entering inside the collection optics area. The apertures 142 will open up when the detection probes 170 containing the collection optics enter the cartridge. The apertures 142 will close up again when the detection probes 170 are removed from the cartridge assembly. The shutter can also be a mechanical covering or window, which opens up when it is interfaced with the instrument's detection optics.

Figure 10:
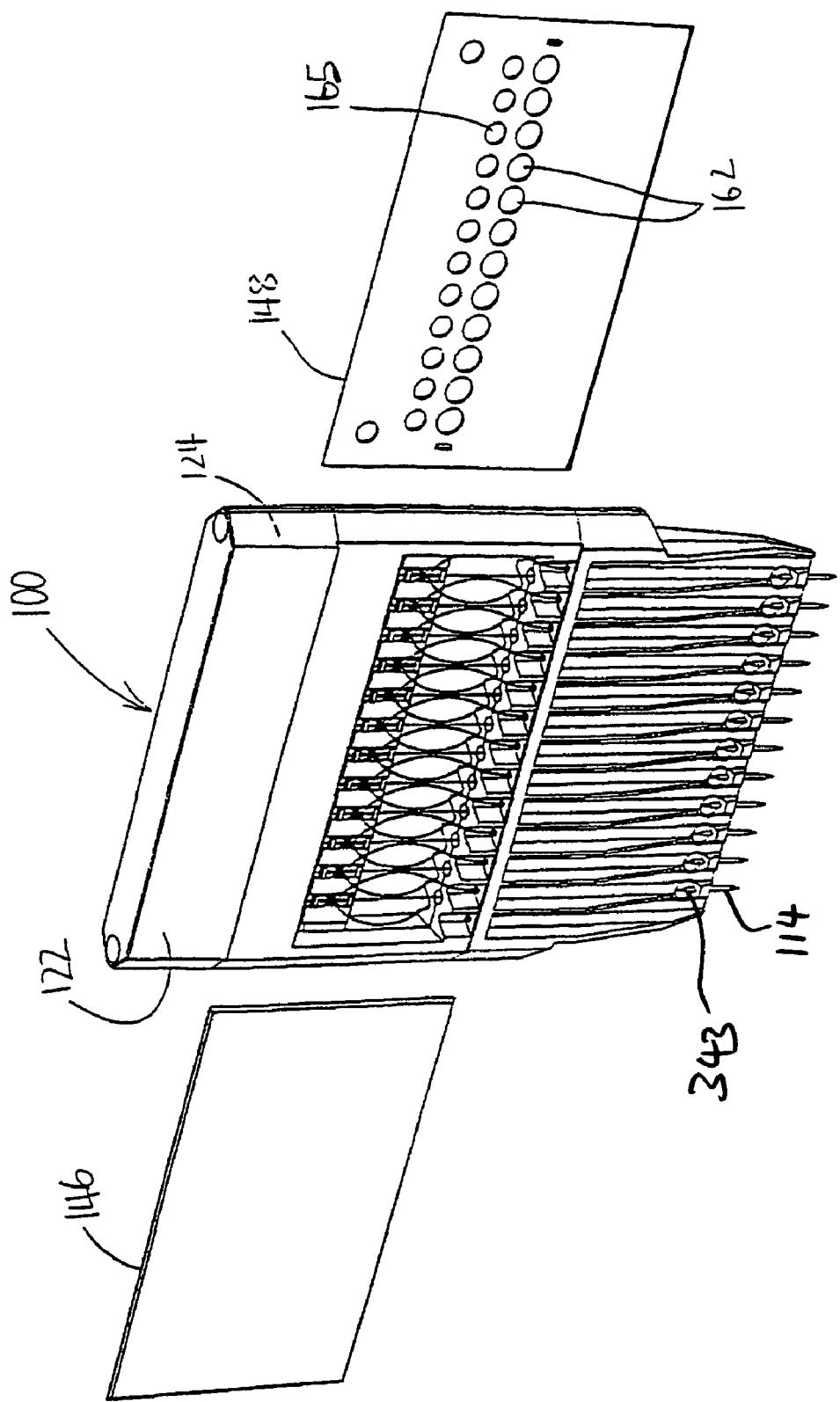
FIG. 10 is a perspective front view of the cartridge mid-section and lower section with the gel reservoir and front and rear covers.

The last stage of assembling the cartridge is shown in FIG. 10 with the front cover 146 and the rear cover 148. The rear cover 148 has holes defining each of the detection optic ports 161. There are also vent holes 165 above holes 162 through which cooled air flows inside the cartridge to cool the capillaries.

Figure 11:
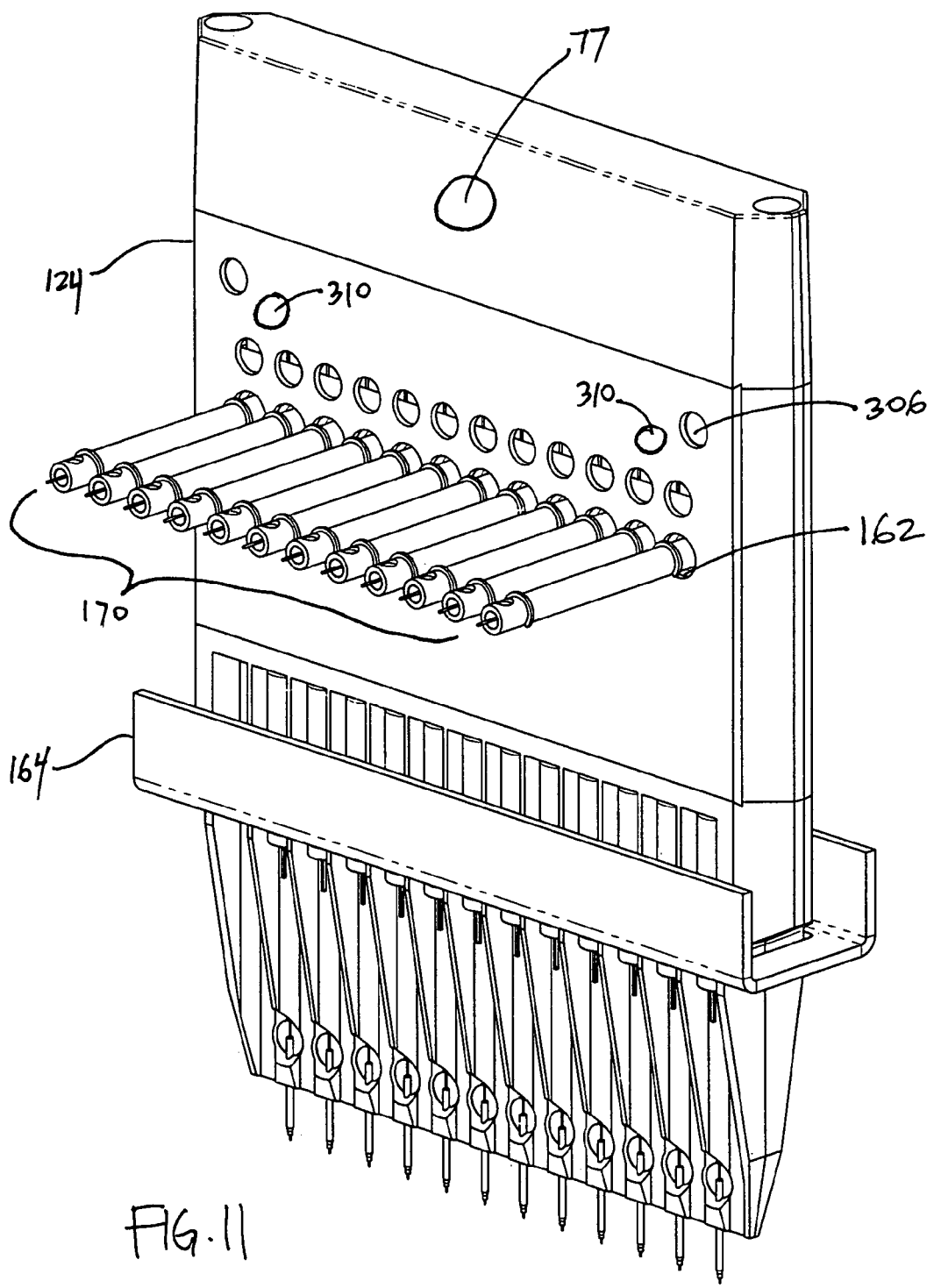
FIG. 11 is a front perspective view of the cartridge with detection optics contained in a closed housing.
Figure 12:
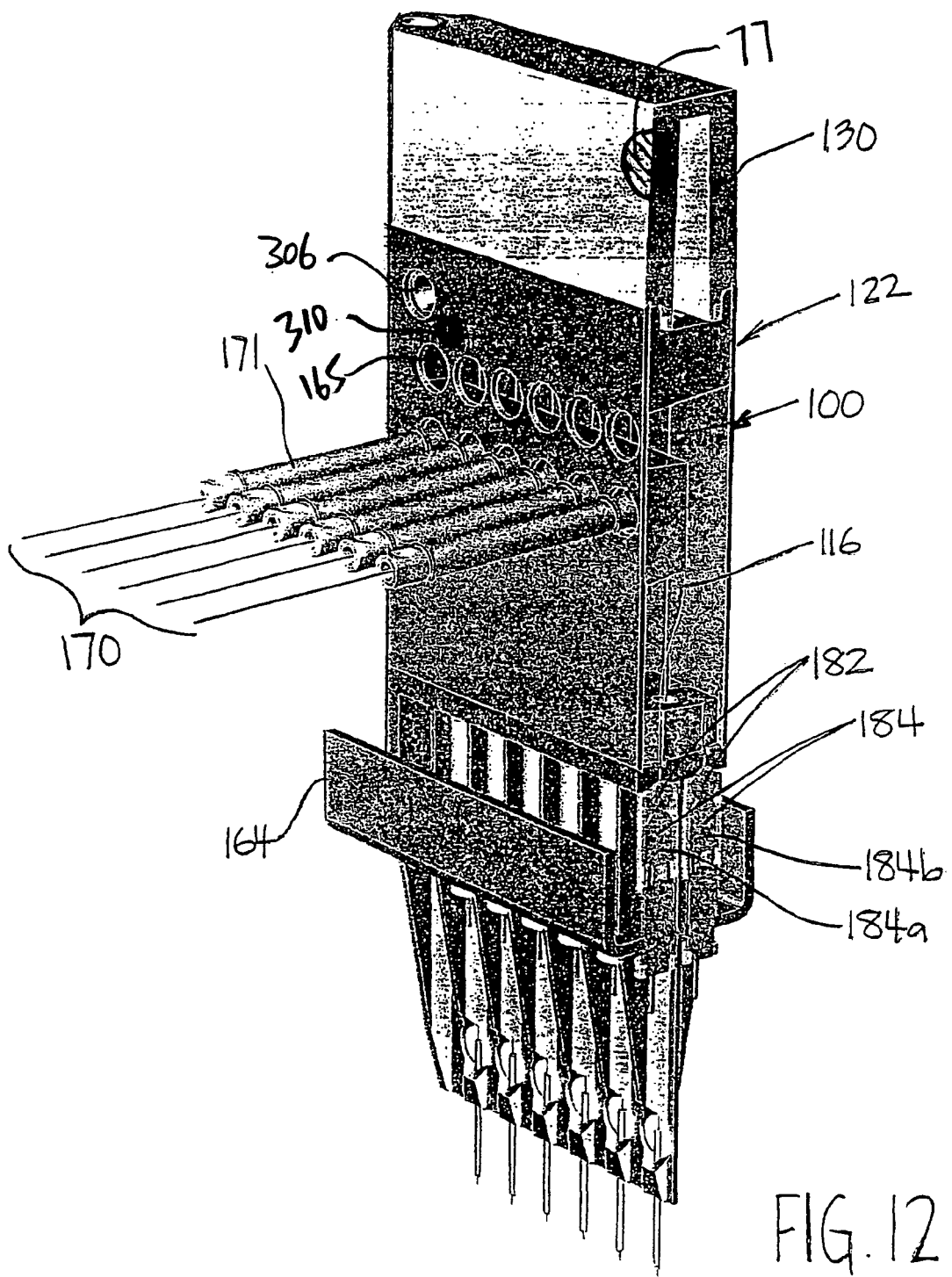
FIG. 12 is a front perspective sectional view of the cartridge in FIG. 11 with the excitation and emission optical system.
Figure 13:
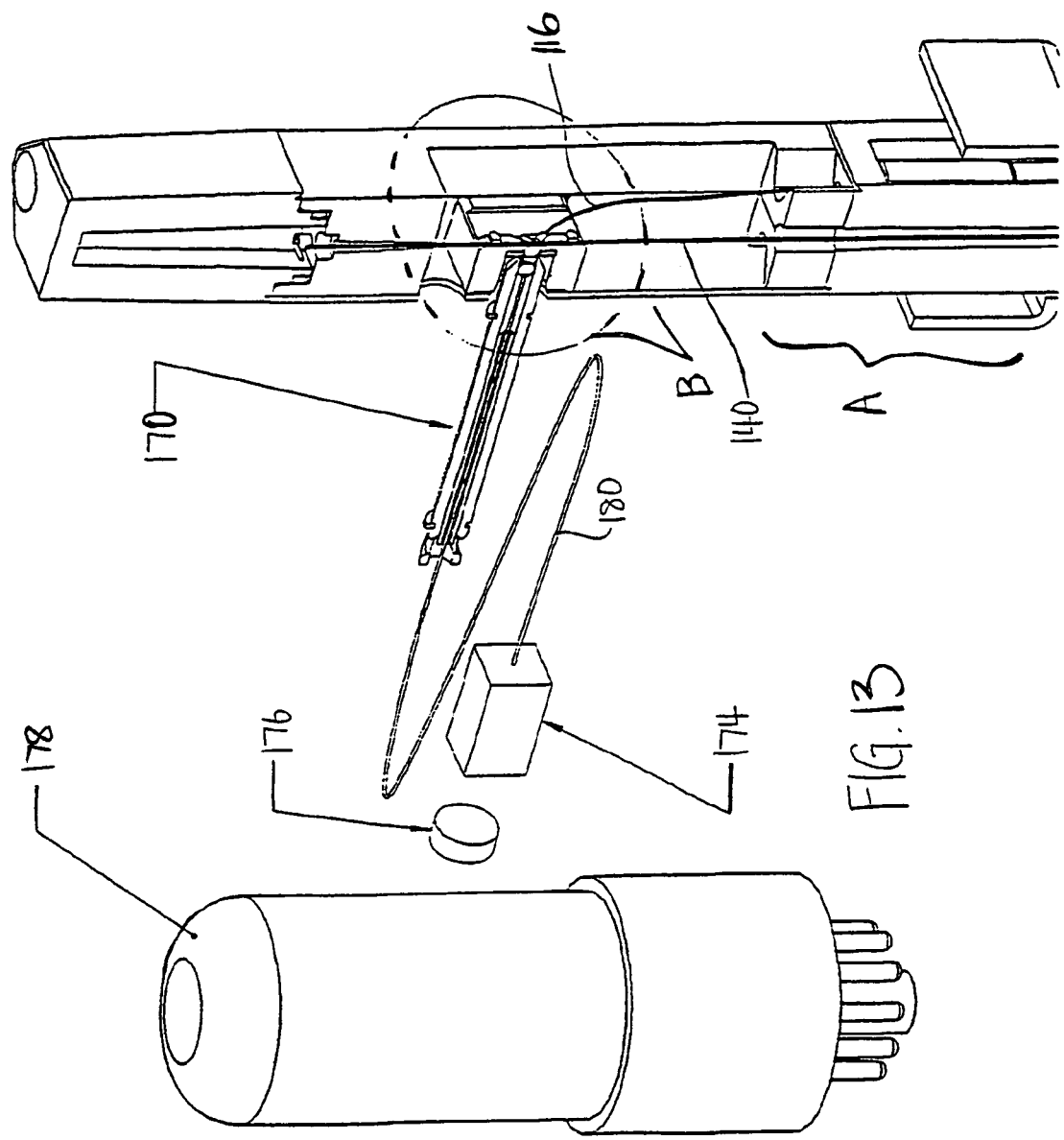
FIG. 13 is a perspective sectional view of the cartridge with schematic of the detector system.

FIGS. 11 and 12 show the rear view 124 of the cartridge 100 with a clearer view of the emission detector probes 170. FIG. 12 shows that the lower-section body 110 is symmetrical, front and rear (i.e., see mirrored LEDs 184*a* and 184*b*). FIG. 13 shows a perspective sectional view of the cartridge 100 with a detector probe 170 coupled to a single photomultiplier tube (PMT) 178 through a fiber connector 174 and an emission filter 176.

Figure 14:
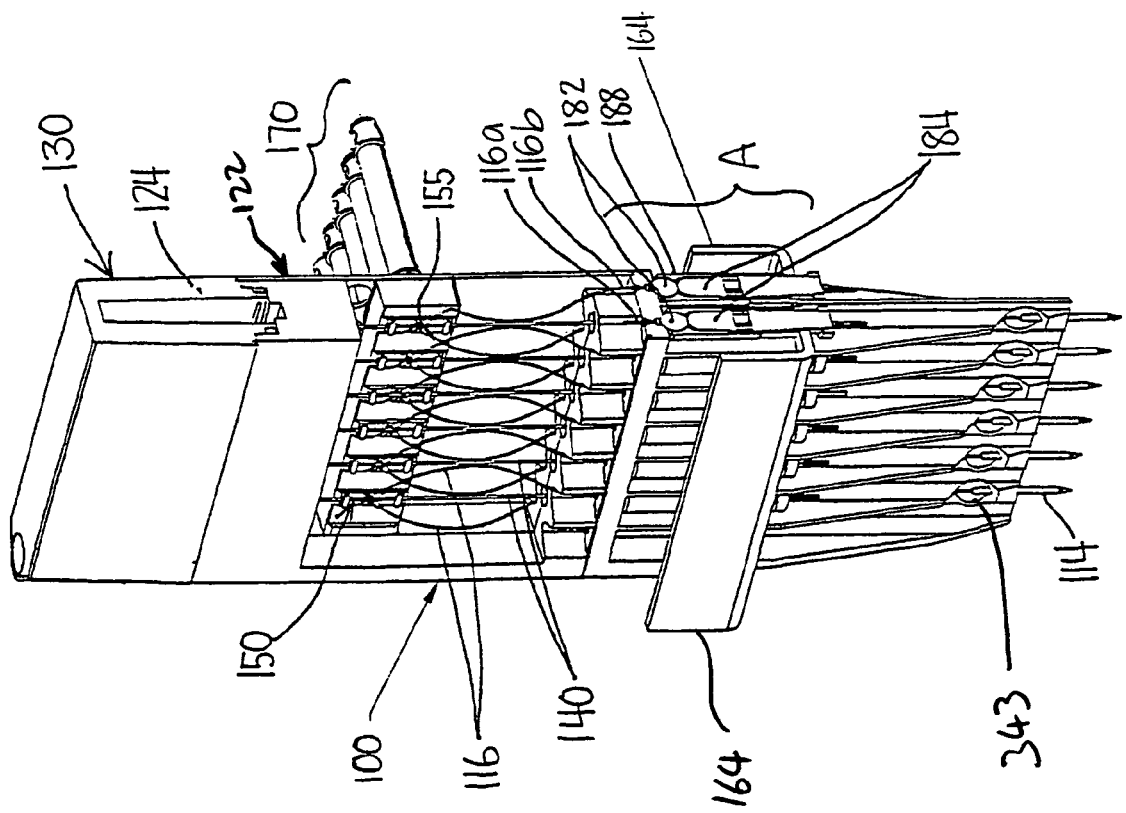
FIG. 14 is a front perspective sectional view of the cartridge with the excitation and emission optical system.

FIG. 14 shows a sectional view of the cartridge 100 along with the excitation and emission optical systems. The cartridge 100 is supported by a support frame 164 (see also FIGS. 22 and 26) found in the interface mechanism 300. The cartridge when installed inside the instrument through this support frame 164 in the interface mechanism 300 gets mechanically aligned with LED module/barrel assemblies. The structure of the lower body of cartridge 110 provides the optical alignment means or coupling of lens barrel assembly 188 to the excitation fibers inside the cartridge. The excitation system includes the coupling micro-ball lenses 182 with respective LEDs 184. The excitation light from the LEDs 184 is directed through the excitation fibers 116 to the detection zone 155 of the capillaries. The emission system includes the emission collection fiber array 170, which is connected at the rear side 122 of the cartridge 100.

Figure 19A:
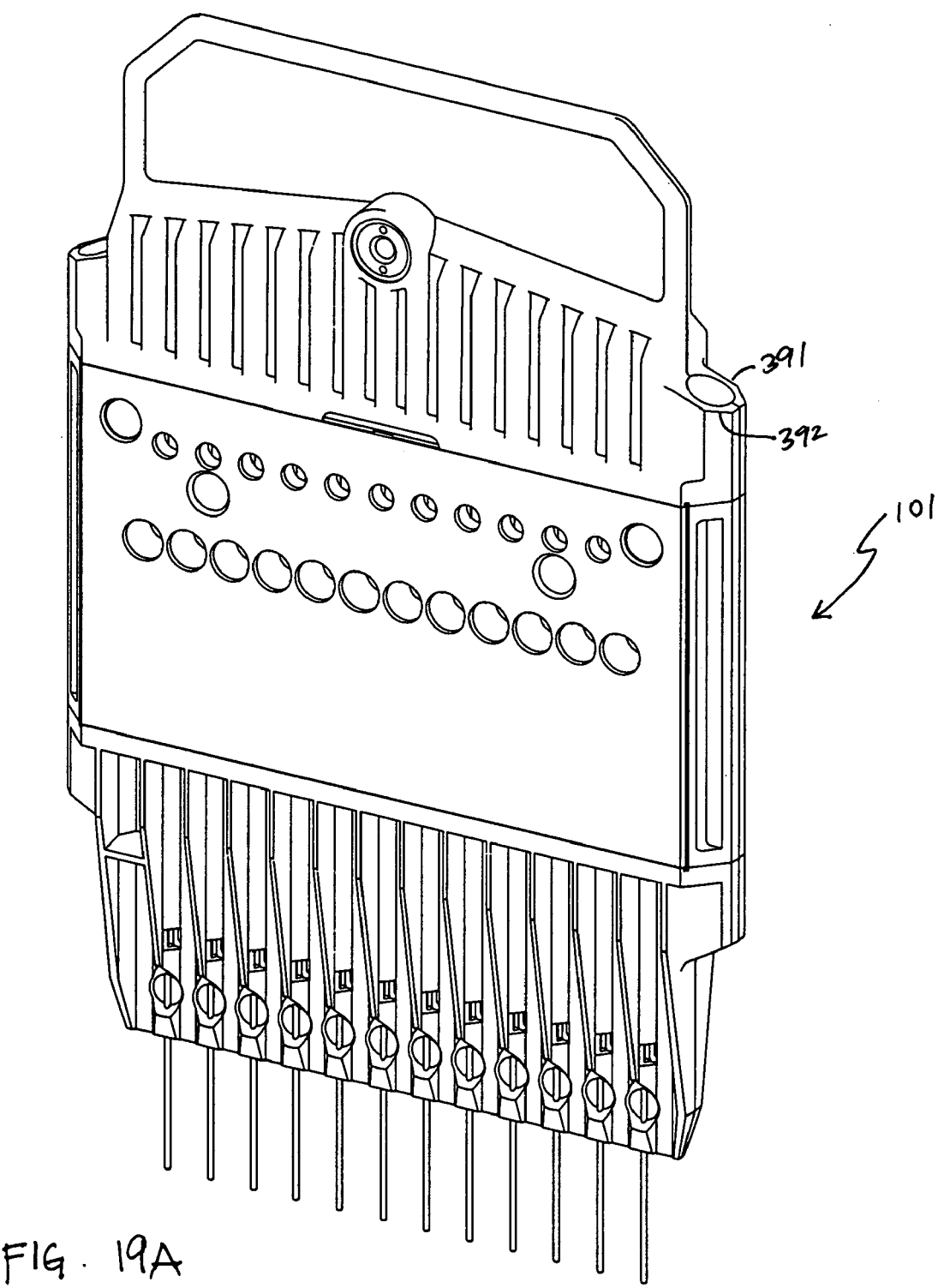
FIGS. 19A and 19B show the external structure of a cartridge in accordance with another embodiment of the present invention.
Figure 19B:
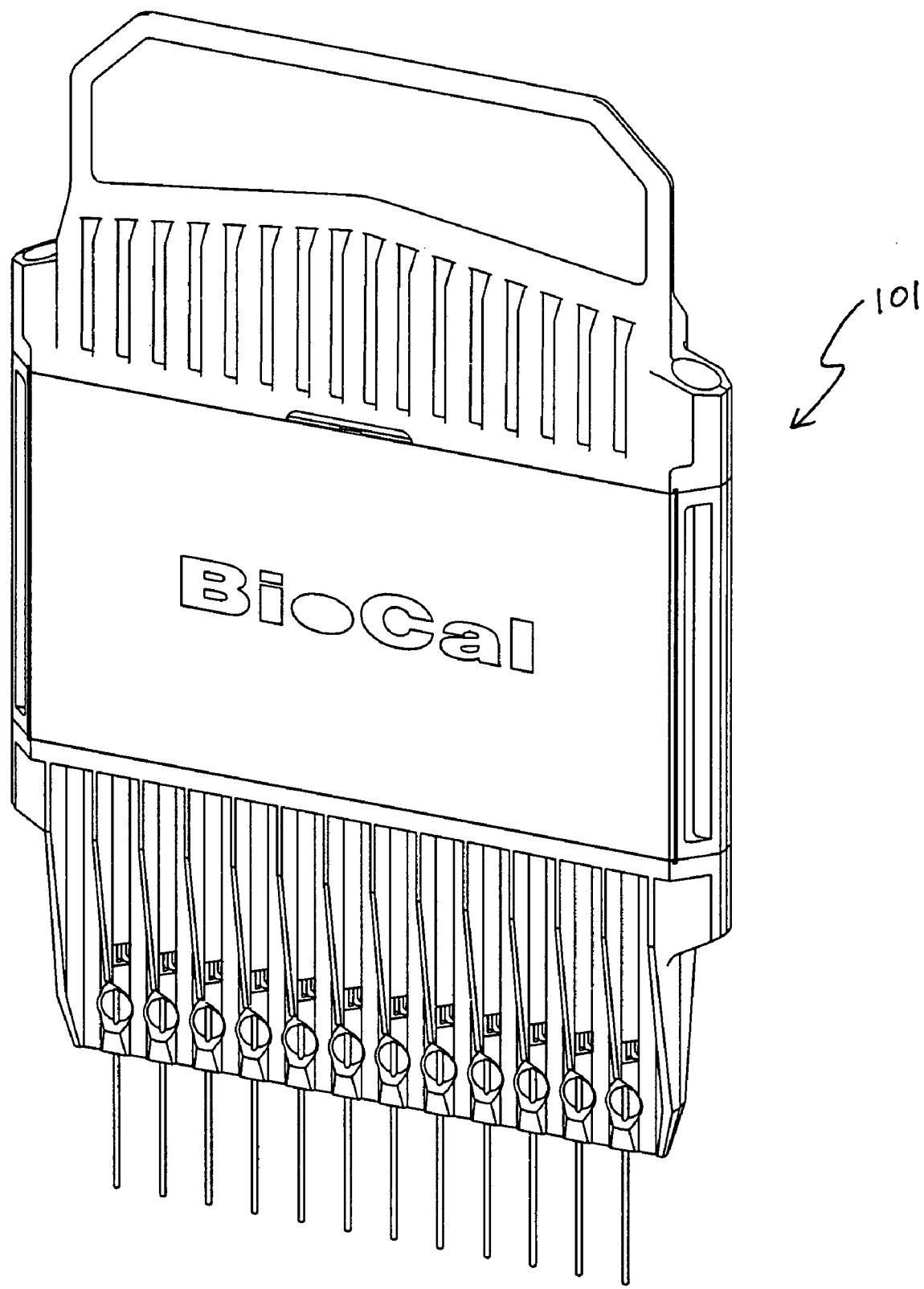

FIGS. 19A and 19B shows the external structure of a cartridge 101 in accordance with another embodiment of the present invention. The functional features and structures of this embodiment of the cartridge 101 are quite similar to those of the cartridge 100 described in the previous embodiment.

Excitation System

Figure 15:
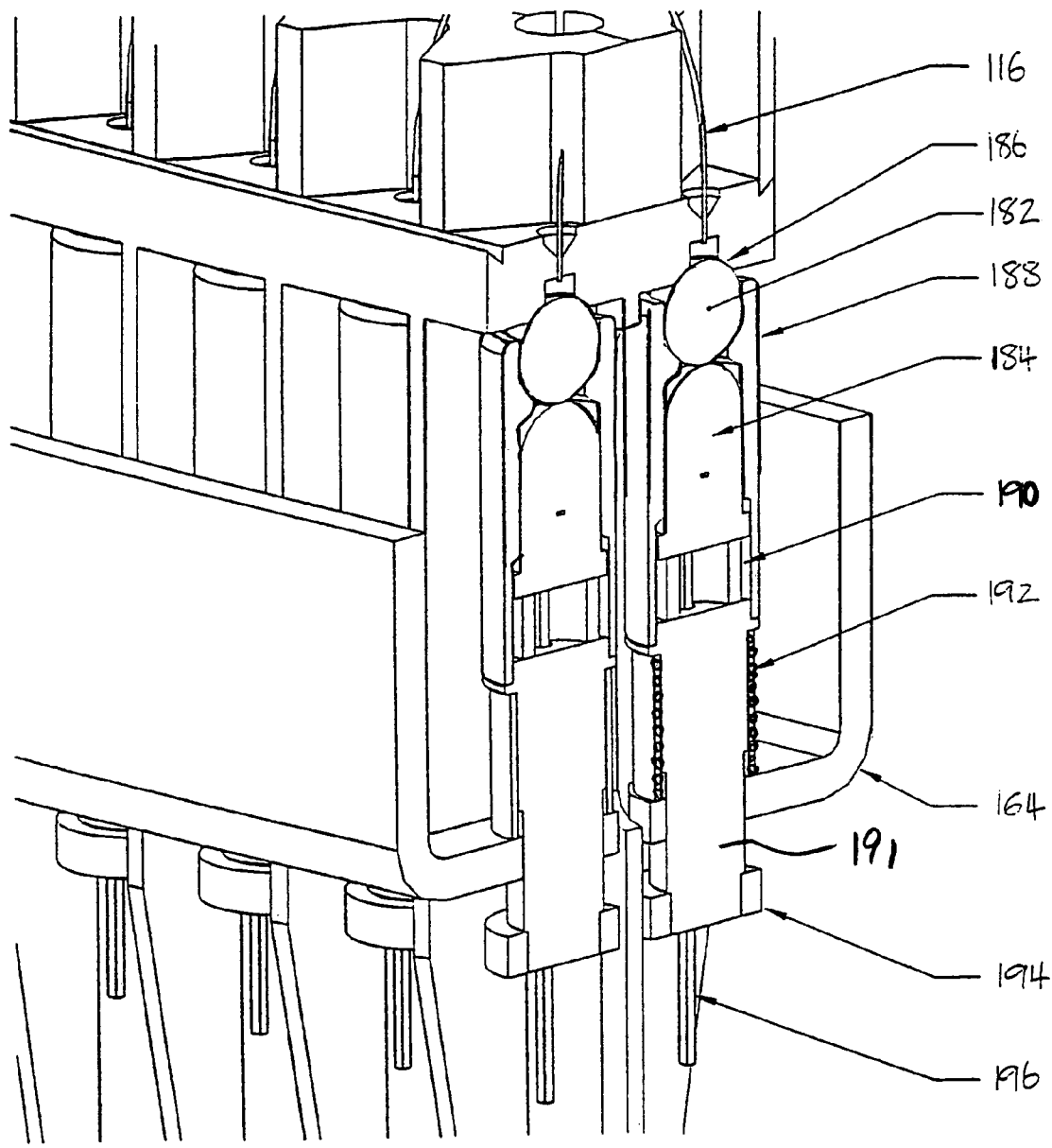
FIG. 15 is an enlarged view of section A in FIG. 14 and a perspective sectional view of the cartridge section A shown in FIG. 13.

FIG. 15 is shows in greater detail section A in FIG. 14. A perspective sectional view of the cartridge section A is shown in FIG. 13. The excitation system is supported by the excite support frame 164, which is fitted to the cartridge (in FIG. 10) during use (as shown in FIG. 11). Since the excitation fiber 116 must receive light and direct light along its path toward the capillary detection zone 155, the excitation system is configured to allow the required light to enter excitation fiber 116 through a ball lens 182 from LED 184. The excitation system includes ball lens 182, LED 184, and elastomer spring 190, which are all arranged within lens barrel 188. A piston 191 supports the lens barrel 188. The piston is supported by and free to move axially against a coil spring 192 on the support frame 164. A retainer 194 is provided at the end of piston 191. LED lead 196 is threaded through piston 191. Within the lens barrel 188, the elastomer spring biases LED 184 against ball lens 182. The coil spring 192, which rests on the excite support frame 164, provides axial and angular compliance in the lens barrel 188, thus allowing ball lens 182 to center accurately in conical lens seat 186. Both these biasing forces provide a closer contacting path for the excitation light to travel, from the LED 184 through the ball lens 182 to the excitation fiber 116.

Two excitation fibers 116 for two wavelengths (for each capillary) are integrated inside the cartridge 100, with fixed alignment, at close proximity to the capillary detection zone 155. These two excitation fibers 116 are coupled to two LEDs 184 (e.g., two different colors: 526 nm and 473 nm) when the cartridge is installed inside the CE system 200 (i.e., DNA Analyzer). Two colors can be separated and detected by two-color emission filters at the detection module (PMT module 178). The cartridge 100 can have single color capabilities for DNA fragment analysis applications and also can be upgraded to have two-color detecting capabilities for other applications.

Detection System

U.S. patent application Ser. No. 10/060,052, which had been fully incorporated by reference herein, is more specifically directed to the time staggered/multiplexed detection scheme that can be adopted in the CE system 200 in which the cartridge 100 is designed to be used.

Figure 16:
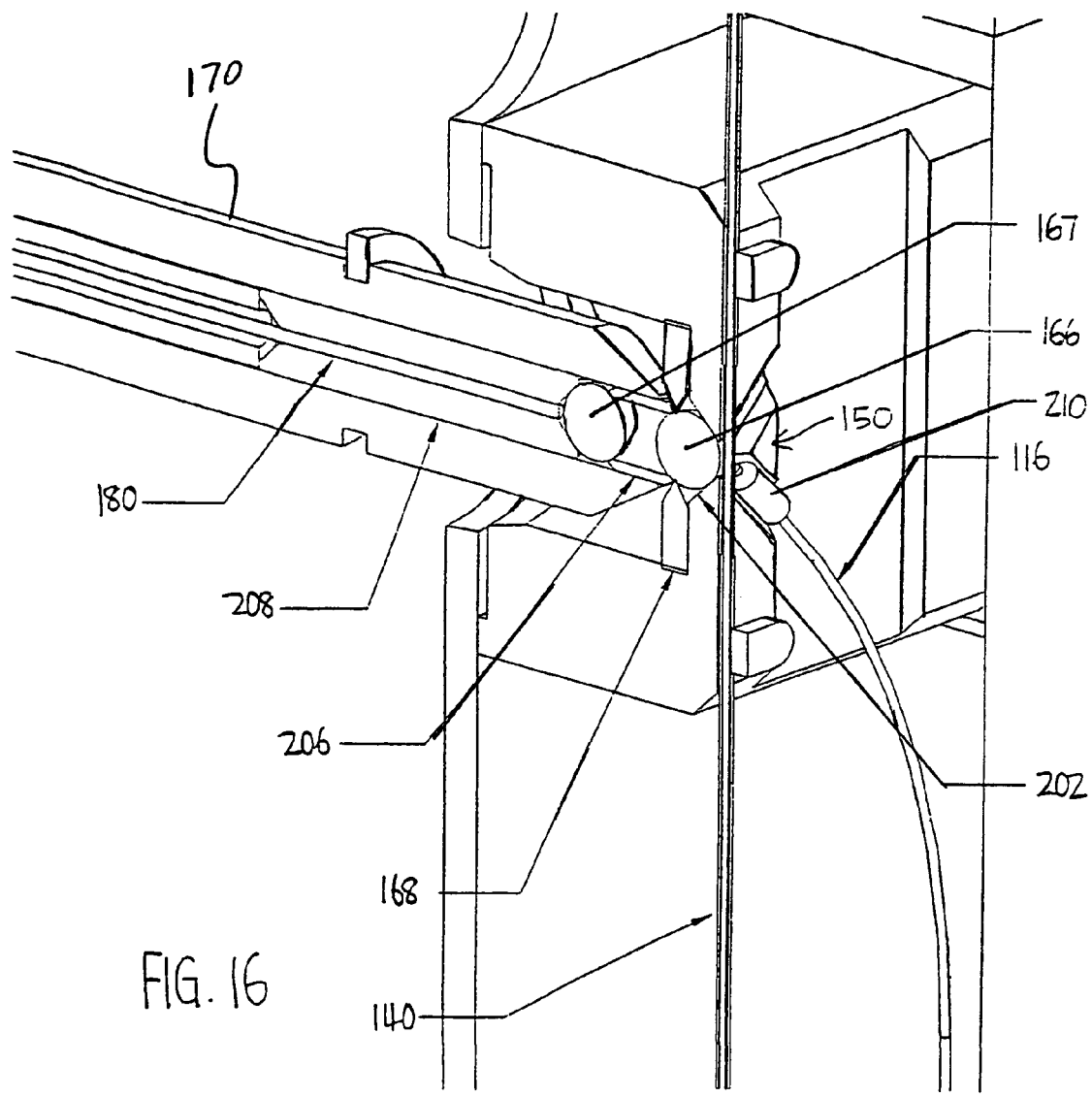
FIG. 16 is a perspective sectional view of the cartridge section B shown in FIG. 13.

FIG. 16 shows in greater detail the detection, or emission, section B in FIG. 13. Excitation light from a light source (e.g., LED 184) travels in the excitation fiber 116 to the detection zone 155 of the capillary 140. A fiber ferrule 210 strengthens and protects the excitation fiber 116 that is inserted within V-groove block 150. Two excitation fibers 116 may be guided to one V-groove block 150, both directing light from the two lower angle openings of the V-groove block. (U.S. patent application Ser. No. 10/319,803 discloses in greater detail additional embodiments of detection optics to the capillary.) The preferred embodiment for aligning each excitation fiber with a capillary is a single block featuring machined V-grooves that nest both the capillary and the fiber in precise alignment to each other. The block may be manufactured by using tooling for a coined part or by injection molding. Also, a cross drilled screw machine part may be used in which the capillary and fibers would be loaded in precisely machined holes rather than in V-grooves.

Figure 17:
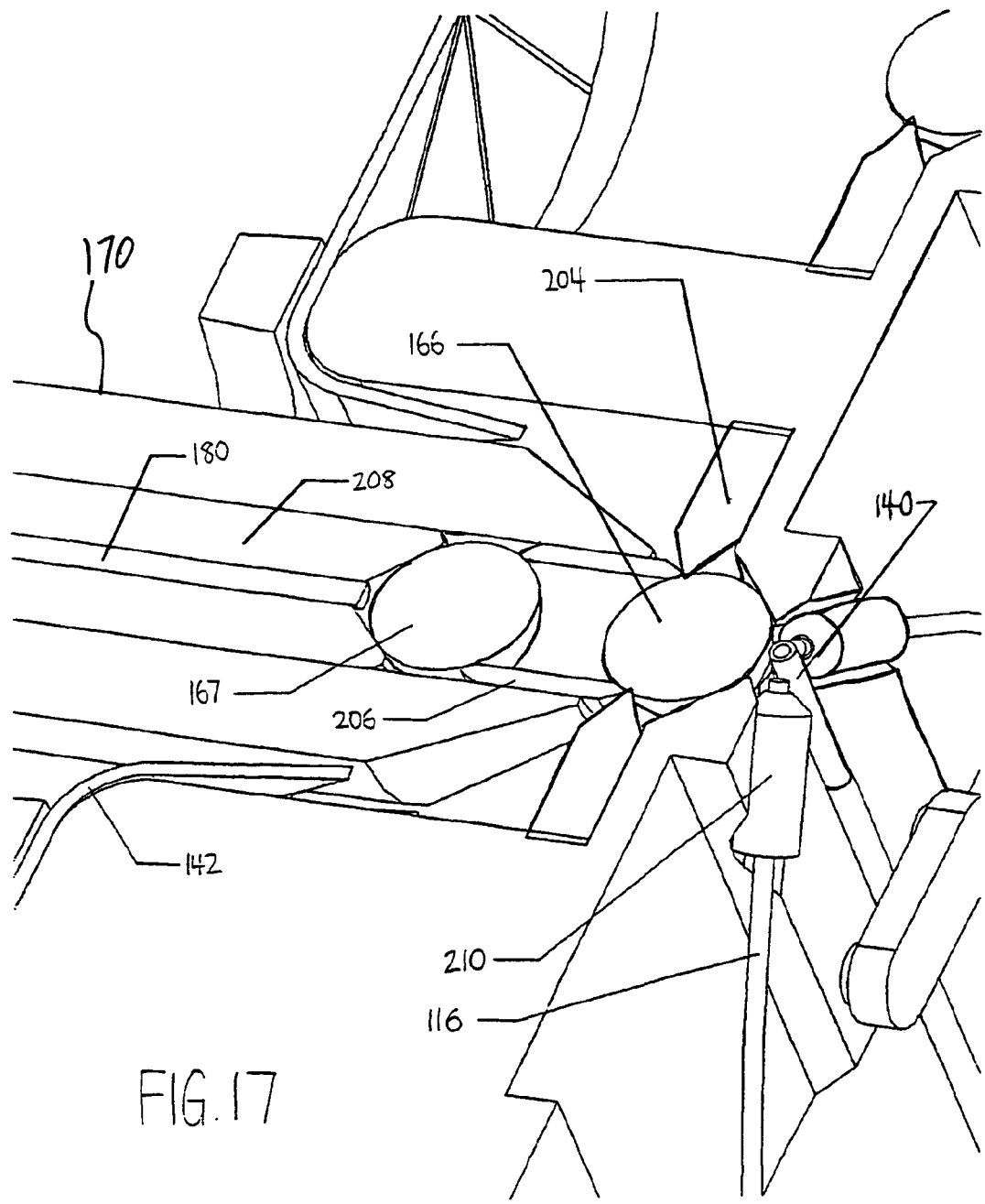
FIG. 17 is perspective sectional view of the detection zone with lens, probe, capillary, and excitation fiber.

When the excitation light is directed at the detection zone 155 (also see FIG. 17), the detection system detects emitted light, or emission signals at 90 degrees with respect to the excitation plane. Collimation optics for collimating the emission beam is needed since the emission fiber 180 is outside the liquid or gel. The Numerical Aperture of the excitation fiber 116 determines the amount of power density launched inside the gel close to the detection zone. The excitation light source may be a LED 184, which is relatively inexpensive, or a laser (may be a solid state laser, gas laser, dye laser or the like). The florescence emissions from the separated components or analytes at the detection zone is collected through micro-lenses 166 and 167, and directed through an emission collection fiber 180 to a detector. The fiber 180 is held in place by a ferrule 208 in the detector probe 170. As will be described below, the detector probe 170 is actuated by the interface mechanism 300. Between these two ball lenses 166 and 167 is a spacer 206. Alternatively, a single ball-lens coupling may be adopted. The capillary 140 may have transparent walls, or opaque walls provided with a transparent window to direct emissions to the micro-lenses 166 and 167 (or alternatively using a single micro-ball lens 166). The lens 166 is used for collecting emissions and preferably has a high collection angle property (e.g., a sapphire micro-lens with index of refraction of n=1.76 from Swiss Jewel Company Model # B2.00 that has a short focal distance with a high numerical aperture (N.A.)). The lens 167 is for coupling the collimated emission light produced by the sapphire lens to the emission fiber 180 (e.g., a BK-7 micro-lens, available from the Swiss Jewel Co.). The fluorescent light, which has a higher wavelength (e.g., 570 to 630 nm) than the excitation light, is then routed by a large core optical fiber 180 (370 μm O.D., 0.22 NA fibers, but could also be in ranges of: 100-1000 μm O.D., 0.12-0.5 NA) to the detector 178 (e.g., RS984 Hamamatsu photo-multiplier tube (PMT)) after going through color separation (e.g., using 570-630 nm) long pass emission filters. The emission signals are relayed by emission fibers 180 into the detector module 178, where they are filtered by a single or multiple emission filter 176 and are read (detected) in a time-multiplexed (time-staggered) scheme. The detection fiber 180 can be seen more clearly in connection with the detection optics system as described and shown in FIG. 13.

Interface Mechanism

The interface mechanism of the present invention accomplishes quick and reliable interface connections to the disposable gel contained capillary cartridge 100. These interface connections include an gas pressurization connection, high voltage connections, and precision optical connections. The interface also provides precise and repeatable mechanical positioning of the cartridge, to accurately position the components of the cartridge in relation to the support elements in the CE system 200, including positioning the capillary tips in relation to external sample or buffer reservoirs, found on 96-well titer plate, for example. Additionally, the interface provides separate electrical and optical connections to each separation channel, thus providing channel-to-channel isolation from cross talk both electrically and optically and insulation to the rest of the instrument from high voltage.

One aspect of the present invention provides an interface mechanism that precisely positions the cartridge in relation to the support elements (e.g., high-voltage, pressurize gas, incident radiation and detector) provided by the supporting instrument, and makes automated, reliable and secured alignments and connections between various components in the cartridge and the support elements in the instrument. Such alignments and connections are reliably implemented, in a reliable automated sequence, after the cartridge had been securely received by the interface mechanism.

In another aspect of the present invention, the interface mechanism comprises pneumatically or electro-mechanically driven actuators for engaging structures on the cartridge, to securely connect at least one of gas pressure, high voltage, emission detection optics, and excitation radiation optics. In one embodiment, the pneumatically driven actuators comprise gas driven pistons.

In a further aspect of the present invention, the interface provides separate high voltage and optical connections for each separation channel in the cartridge, thus providing channel-to-channel isolation from cross talk both electrically and optically.

Figure 18:
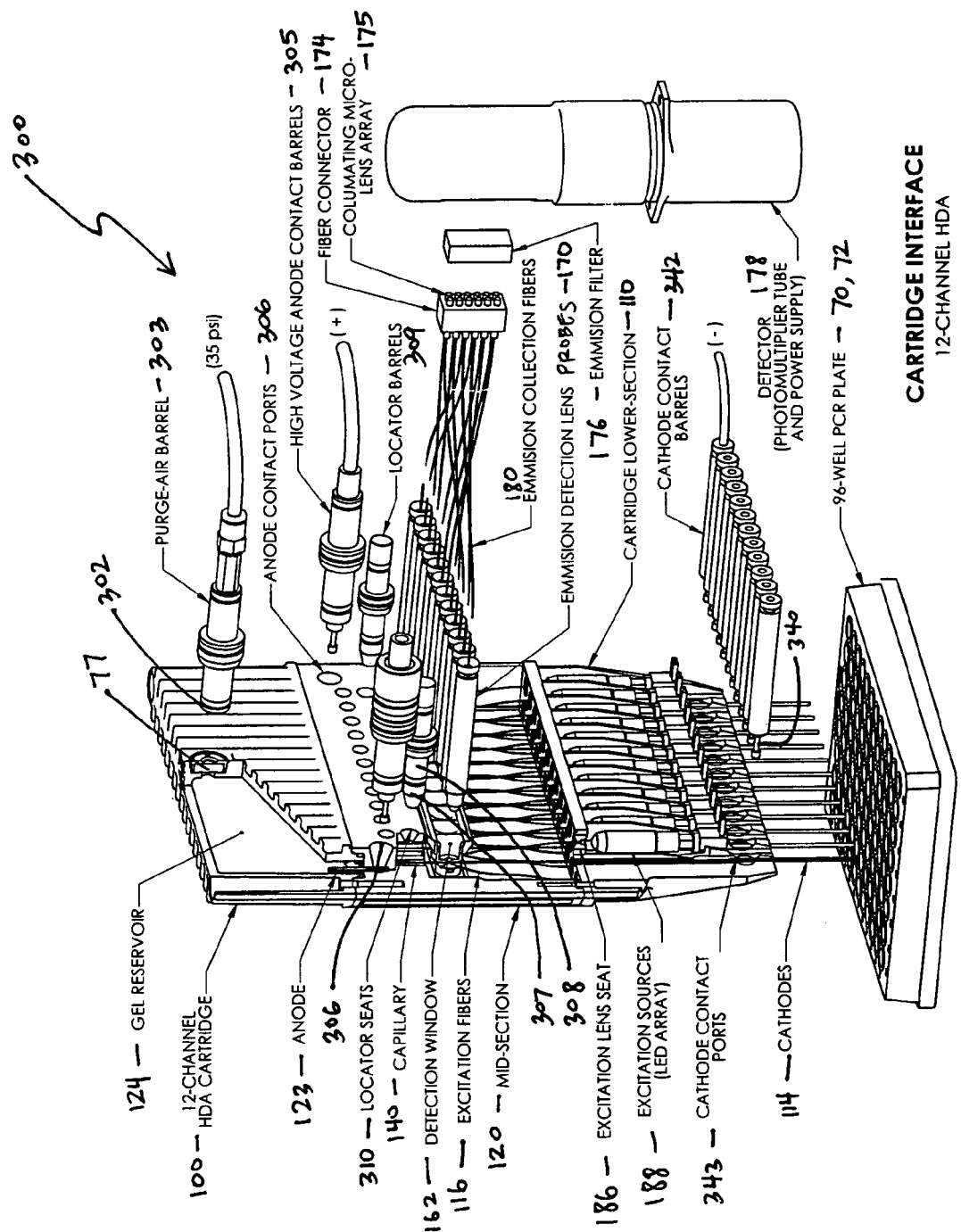
FIG. 18 is a schematic overview illustrating the relationship between the cartridge components and associated components on the interface mechanism.

FIG. 18 provides an overview of the relationship of various cartridge components and the functional components of the interface. In this embodiment, all mechanical actuations are pneumatically driven, an in particular, gas driven by the pressure source 78 (FIG. 2) via appropriate pressure hoses and solenoid control valves, which may be part of the various pneumatic actuators. Pneumatically driven actuators are easier to be integrated into the interface mechanism due to the presence of high voltage lines feeding high voltage current to the cartridge. Electro-mechanical, manual-mechanical, and other actuations are also possible as an alternative, without departing from the scope and spirit of the present invention.

As shown in FIG. 18, the interface mechanism comprises the following active elements that align and engage to associated components in the cartridge:

(a) Purge-air piston barrel 303 provides pressurized gas (e.g., N2) to the cartridge reservoir 130 by o-ring coupling of the purge-air barrel 303 to the reservoir purge hole 77. The purge-air barrel 303 comprises piston that is pneumatically driven.

(b) High voltage anode contacts 304 and barrels 305—Two axially compliant contacts 304 provide high voltage connections to the common anode 134 through anode contact ports 306. The contacts 304 are in the form of spring loaded pogo pins each mounted in pneumatically driven piston barrels 305.

(c) Locator piston barrels 309—Two pneumatically driven piston barrels 309 pushes against the cartridge 100, such that the conical noses 307 mate with conical seats 310 in the cartridge mid-section 120 to precisely position the cartridge 100 in relation to the interface mechanism 300 and the CE system 200.

(d) Excitation source (LED) barrels 188: Twelve barrels 188 (or twenty-four barrels, in the case of two excitation wavelengths per channel), each housing a ball lens 182 coupled directly to an LED 184 within the barrel, are mounted vertically on springs 192 (shown in FIG. 15) in the interface mechanism 300. The springs 192 provide the axial compliance required for passively aligning the ball lenses 182 to mating conical seats 186 in the cartridge lower-section 110, thereby effecting twelve independent excitation optical couplings to the cartridge 100. Radial compliance for each barrel is accomplished by a mounting design that allows angular deflection (Lens Seat 186) of the barrels 188 as the ball lenses 182 enter the conical seats 186 in the cartridge lower-section 110. The LEDs 184 are all spring loaded with elastomer springs 190 in the barrel 188, which provides independently compliant forces to each lens barrel assembly 188 for a reliable and repeatable alignment to the excitation fiber 116 in the cartridge 100. The cartridge has all the proper conical type features (i.e., conical lens seating 186) to accept the elastomeric spring loaded LEDs 184 from the CE system 200. In another embodiment not shown, the LED source barrel 188 may be actuated by actuators such as the pneumatic actuators for the other barrels described herein.

(e) Emission detection probes 170 and piston barrels 320—The cartridge 100 has alignment features to be easily aligned to the micro-optical detection module inside the system 200. Twelve probes 170 each housing a ball lens 166 coupled to an optical fiber 180 (see FIGS. 16 and 17) are supported on a frame 371 (see FIGS. 20, 22, 26) that is mechanically driven by a pair of pneumatically driven piston barrels 320 that provide the parallel actuations of the probes 170 for interfacing the detection ports 160 in the cartridge 100. In one embodiment, the ball lens 166 at the tip of each probe 170 mates to a conical seat at each capillary 140 in the cartridge 100. Each probe 170 is independently compliant both axially and radially, such as by providing an elastomer spring as in the case of the excitation source barrels 188. The distal end of each fiber is coupled to the PMT assembly 178.

(f) Cathode contacts 340 and barrels 342—Similar to the high voltage anode contacts 304, 12 axially compliant contacts 340 provide connections to the twelve cathodes 114 in the cartridge 100 through the cathode contact ports 343. The cathode contacts 340 are each in the form of a spring-loaded pogo pin mounted in a piston barrel 342. All twelve piston barrels are mechanically supported on a frame 373 (see FIGS. 20, 22, 26) that is driven by a pair of pneumatically driven pistons 344 (schematically shown) that provide parallel actuations of the barrels 342 for interfacing to the cathodes 114 in the cartridge 100.

FIGS. 20-32 are perspective design drawings showing the actual structure of the interface mechanism 300 in accordance with one embodiment of the present invention. The interface mechanism 300 generally comprises a front support block 360 and a rear support block 363. The relevant components described above are shown in the figures using like reference numerals. It is noted that in these figures, the sample/buffer wells 70 and 72 are schematically represented in the form of vials.

Figure 21:
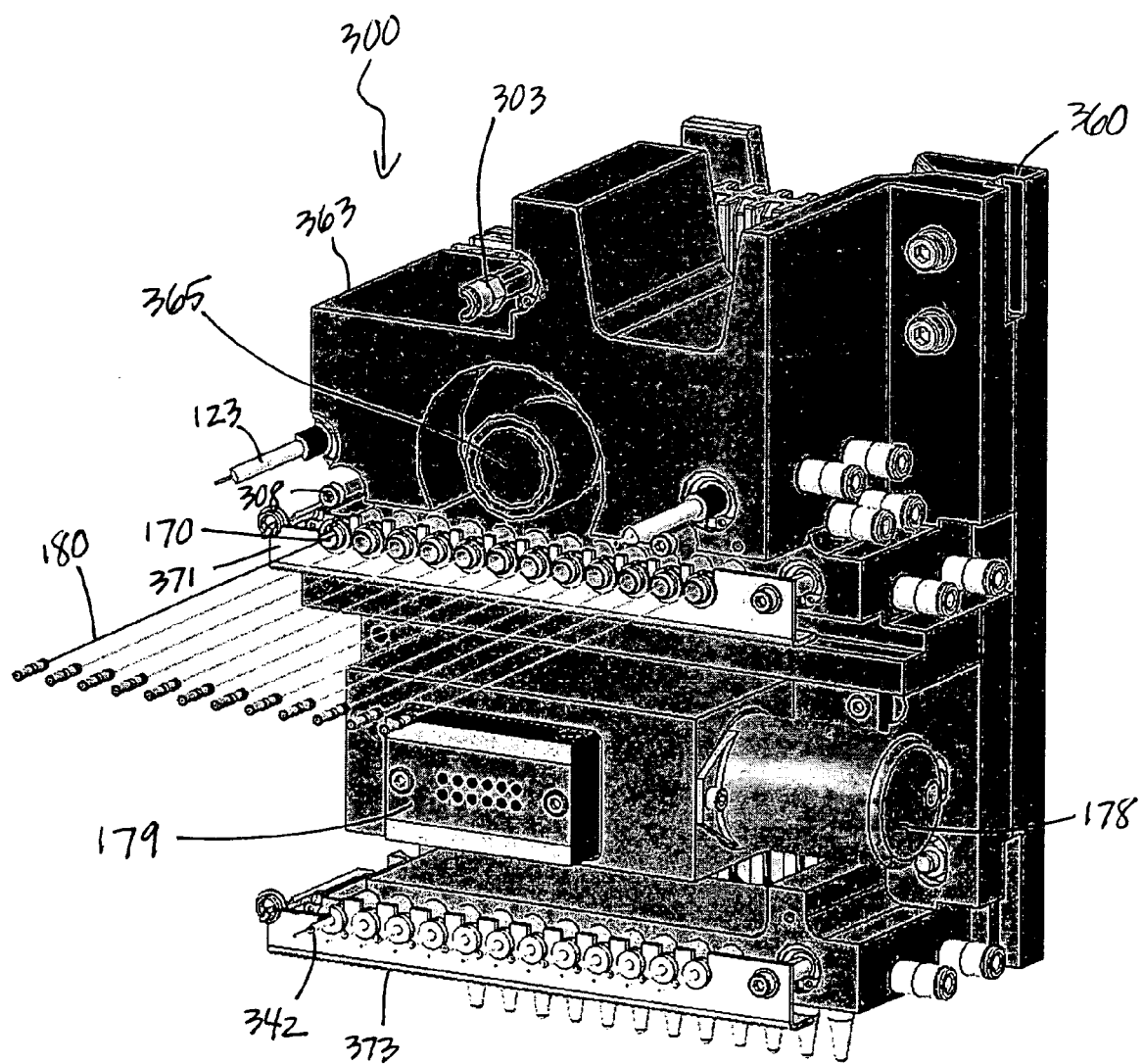
Figure 31:
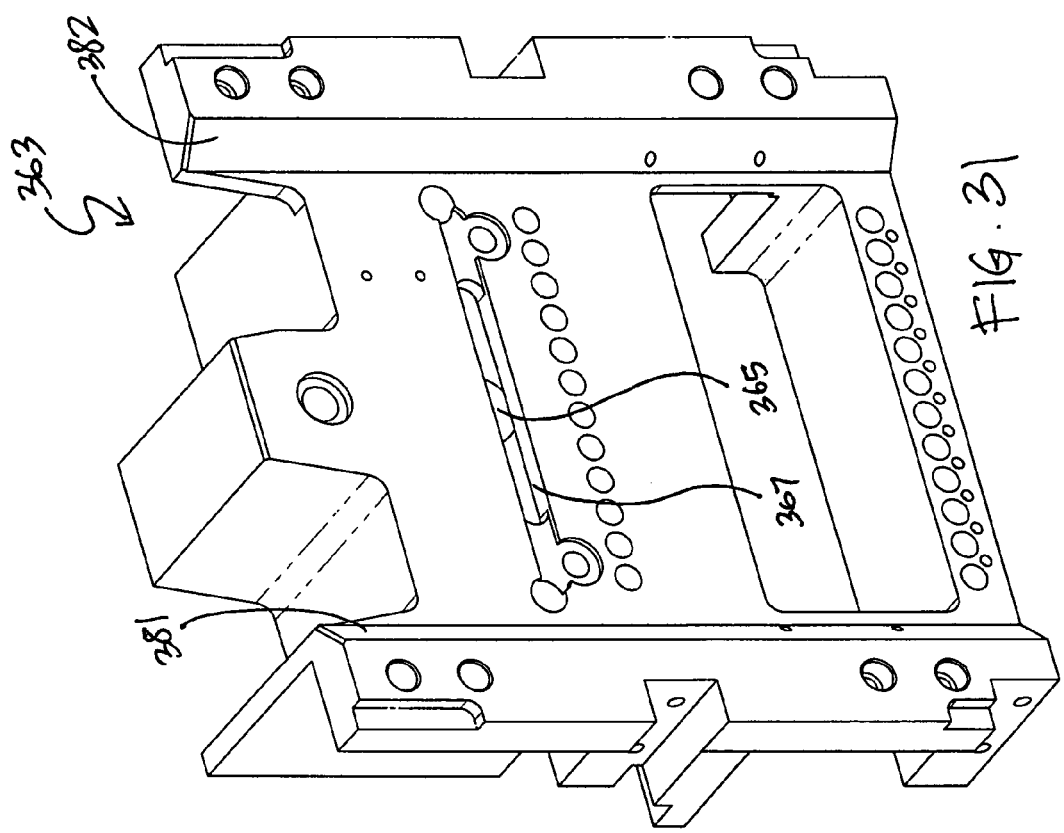
FIG. 31 is a front view of the rear support block of the interface mechanism.

FIGS. 20 and 21 is a rear perspective view of the interface mechanism. In this embodiment, a cooling duct 365 is provided in the rear support block 363 to provide cooling air to the capillaries 140 in the cartridge, via vent holes 165 on the cartridge 100 (shown in FIGS. 10 and 12). Referring also to FIG. 31, the duct 365 expands into a plenum 367 that covers the vent holes 165 on the cartridge 100. The duct 365 is connected to an external duct coupled to a suitable cooling air pump or fan (not shown). Leads 370 extend from the LED source barrels 188. A connector module 179 is provided on the rear support block 363, for housing the collimating microlens array, and coupling to optic fibers 180 to the detection probes 170.

Figure 22A:
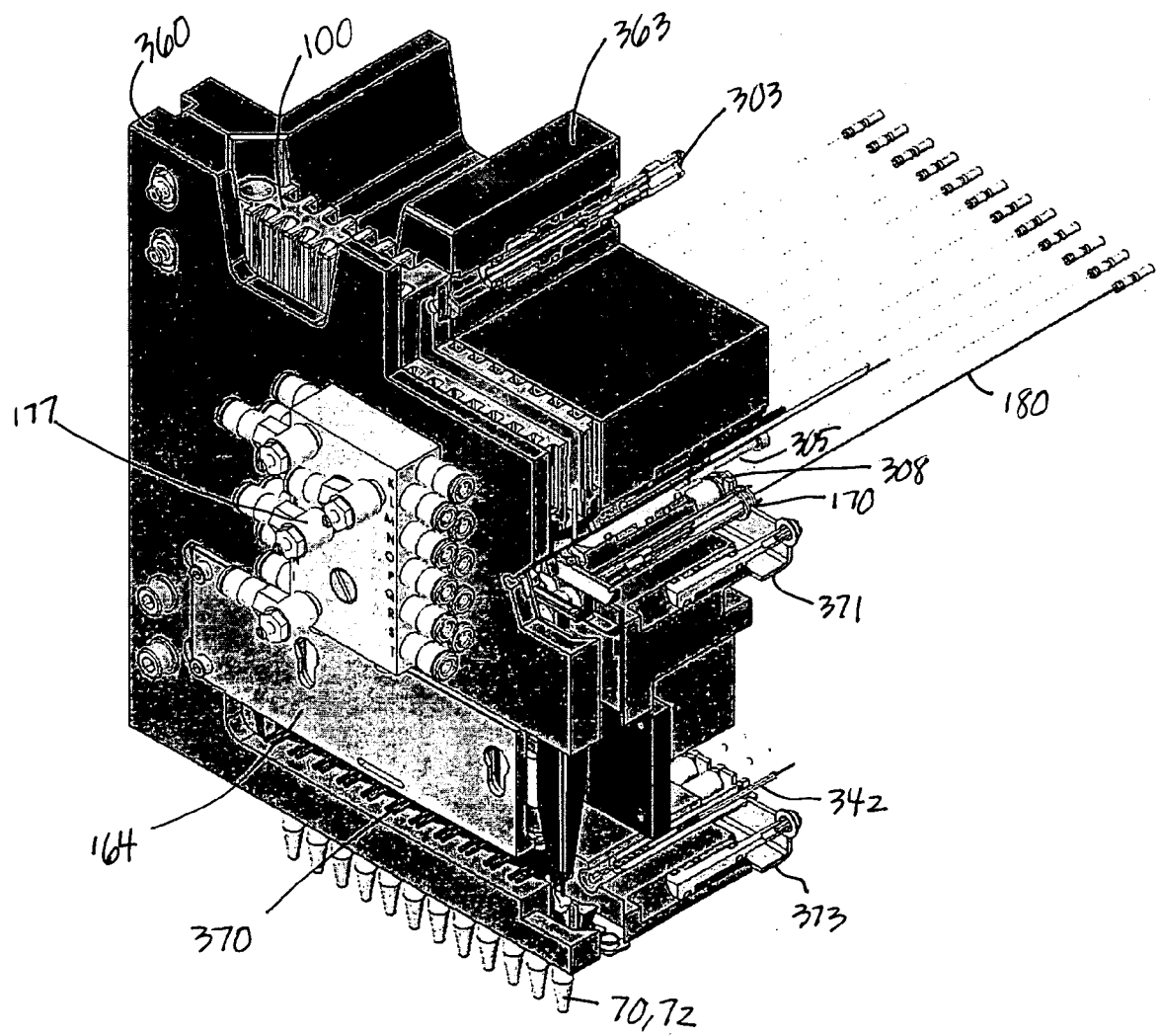
FIGS. 22A and 22B are front perspective views of the interface mechanism.
Figure 22B:
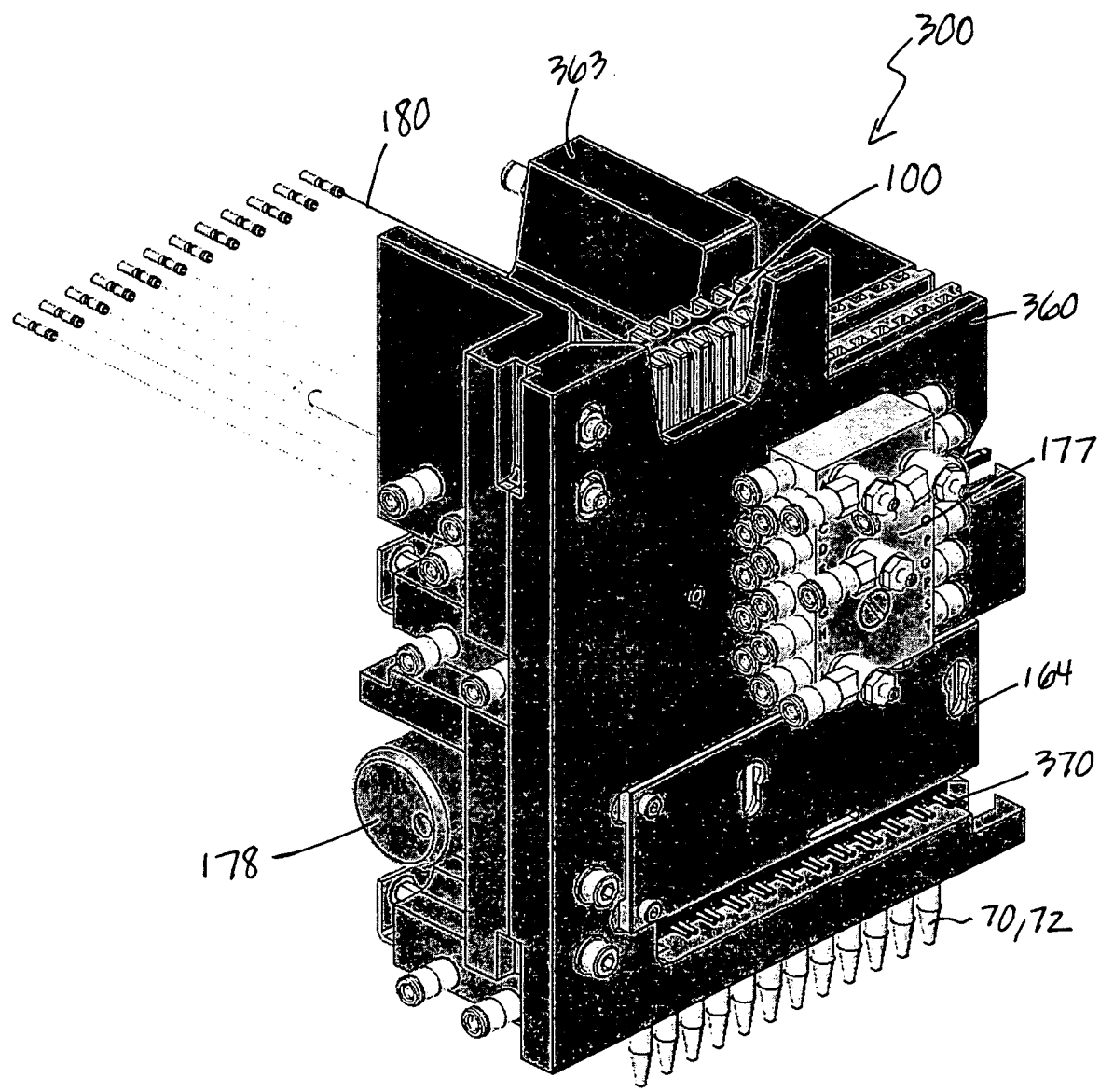

FIGS. 22A and 22B are front perspective views of the interface mechanism 300. A gas manifold 177 is provided on the front support block 360 of the interface mechanism 300, to couple and distribute pressurized gas to the actuators disclosed above. The plumbing includes tubings that are not shown in the figures.

Figure 23:
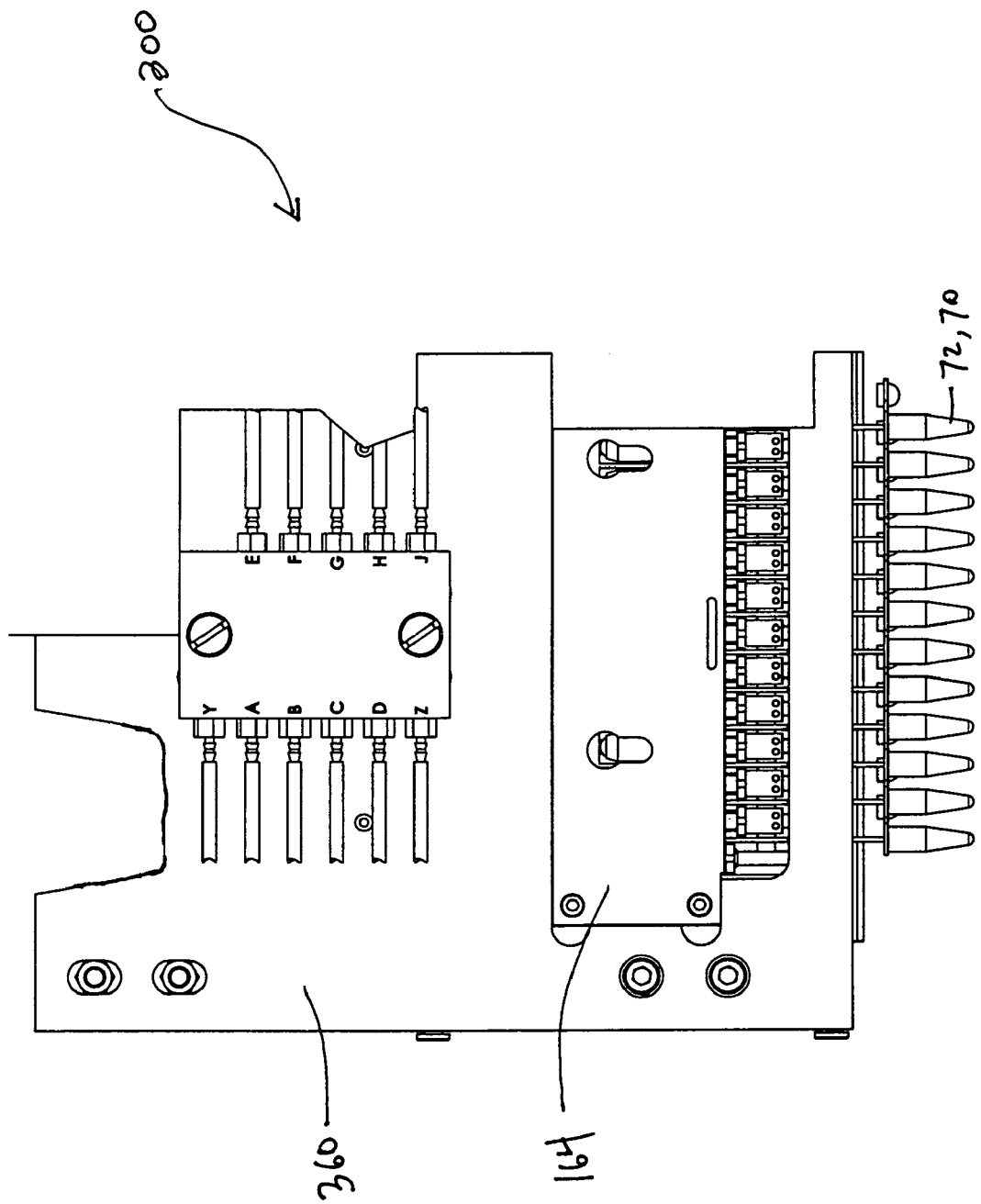
FIG. 23 is a front view of the interface mechanism.
Figure 24:
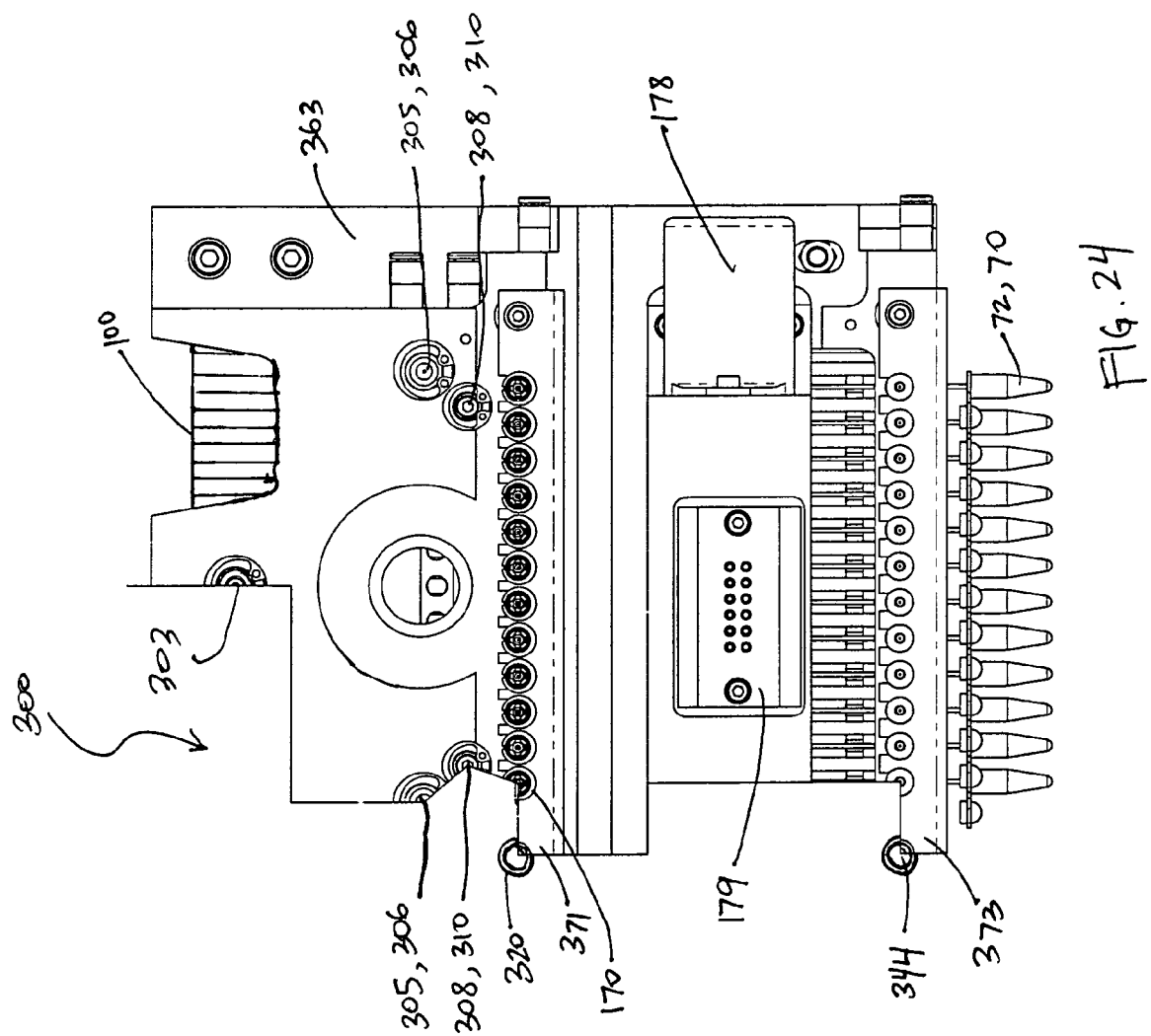
FIG. 24 is a rear view of the interface mechanism.
Figure 25:
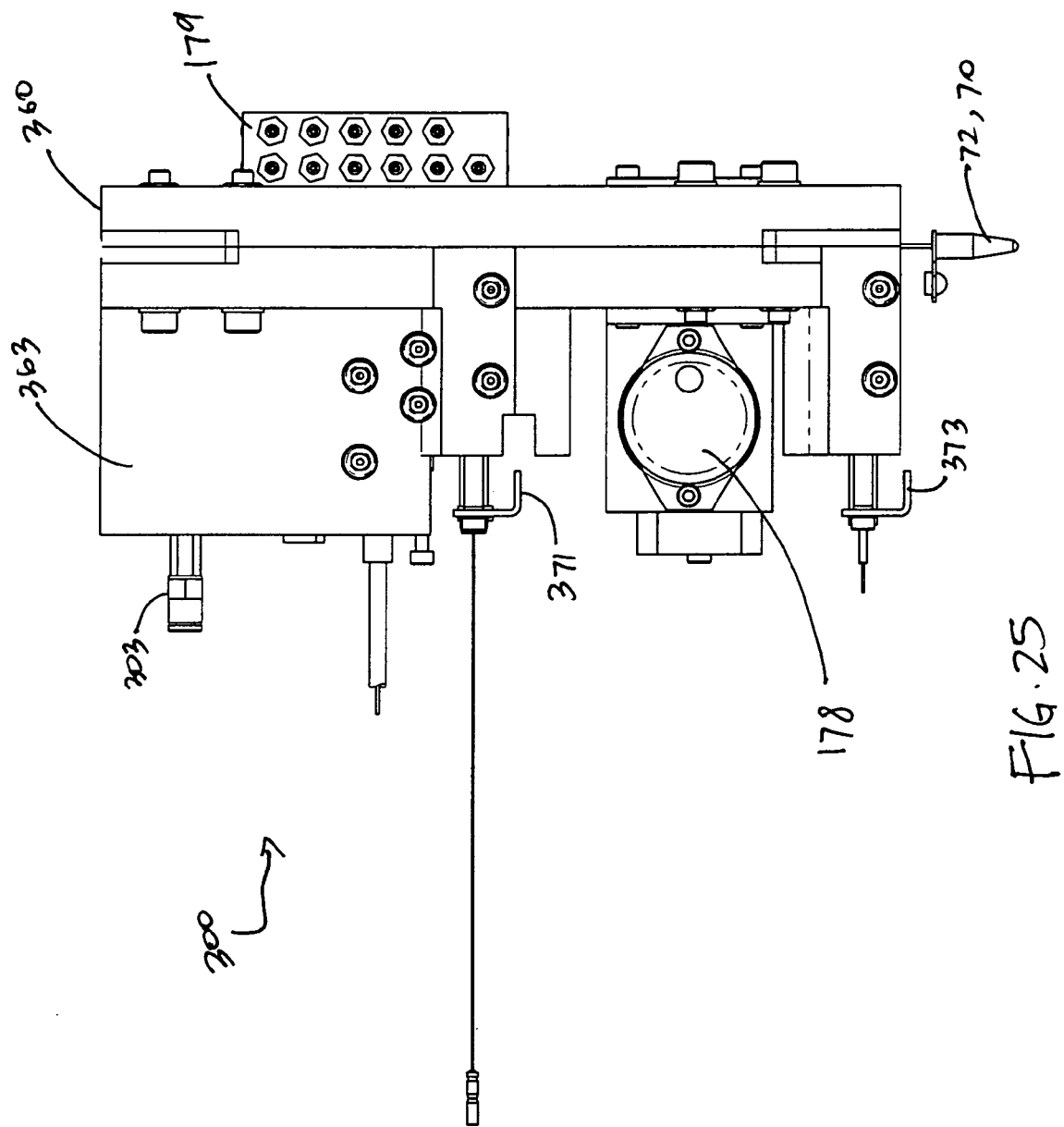
FIG. 25 is a side view of the interface mechanism.
Figure 26:
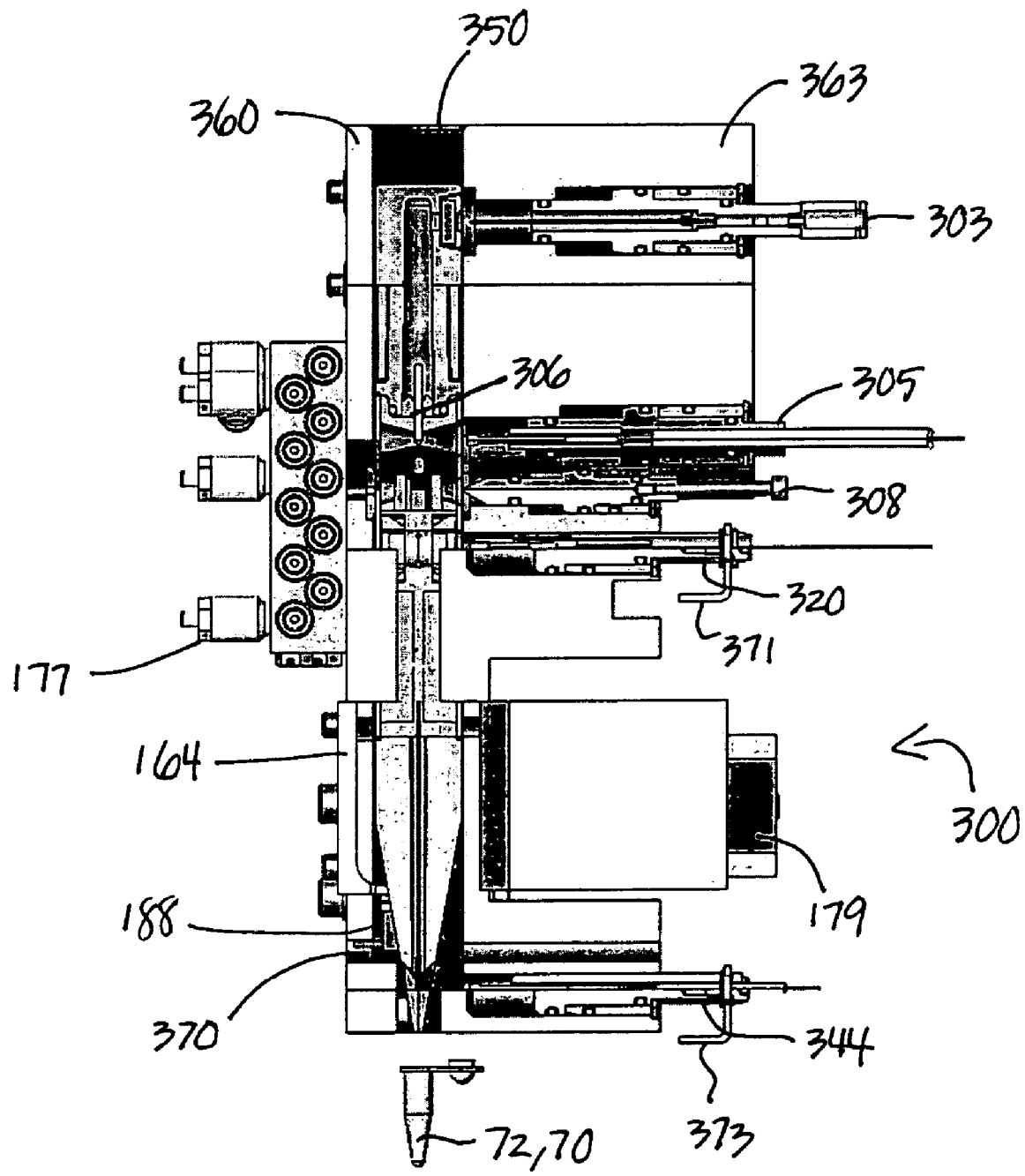
FIG. 26 is a side sectional view of the interface mechanism, taken along line 26-26 in FIG. 28.
Figure 27:
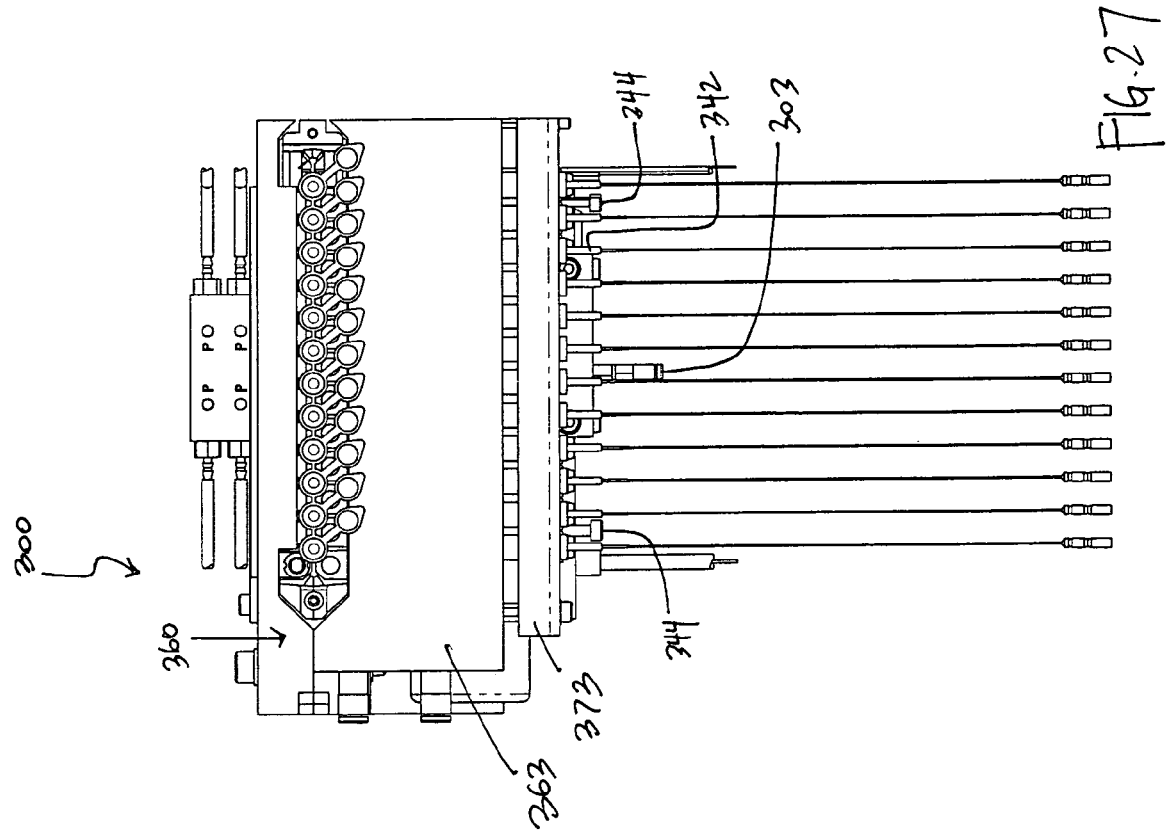
FIG. 27 is a bottom view of the interface mechanism.
Figure 28:
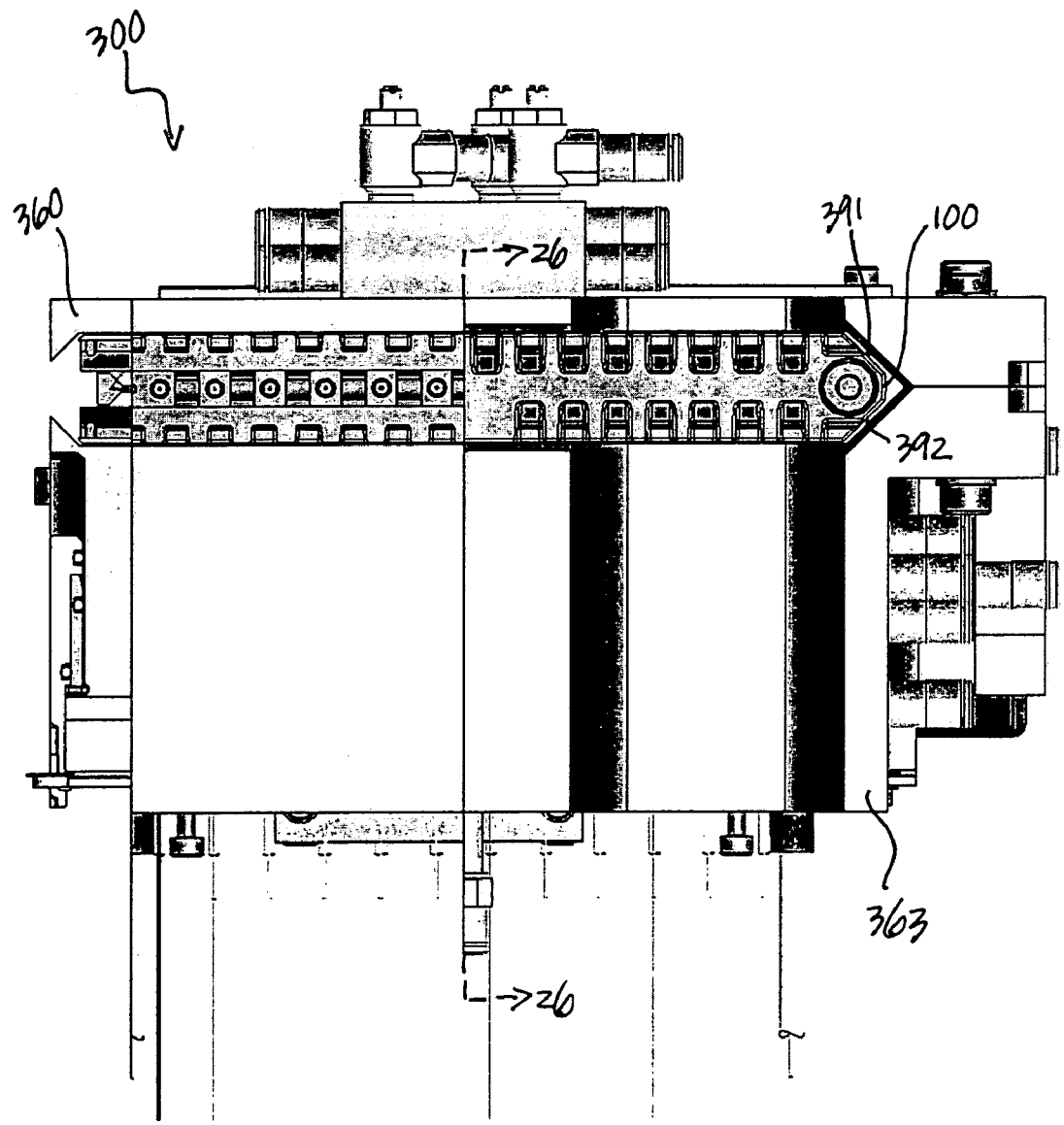
FIG. 28 is a partial top view and top sectional of the interface mechanism, taken alone line 28-28 in FIG. 23, to show the top and bottom halves of the interface mechanism.

FIG. 23 is a front view of the interface mechanism. FIG. 24 is a rear view of the interface mechanism 300. FIG. 25 is a side view of the interface mechanism 300. FIG. 26 is a side sectional view of the interface mechanism 300, taken along line 26-26 in FIG. 28. FIG. 27 is a bottom view of the interface mechanism 300. FIG. 28 is a partial top view and top sectional of the interface mechanism 300, taken alone line 28-28 in FIG. 23, to show the top and bottom halves of the interface mechanism 300. The various views provide additional details to the structure of the interface mechanism 300.

The front and rear support blocks 360 and 363 of the interface mechanism 300 are provided with holes to receive the various barrels and/or actuators described above. The positions of the holes match the associated components on the cartridge 100.

Figure 29:
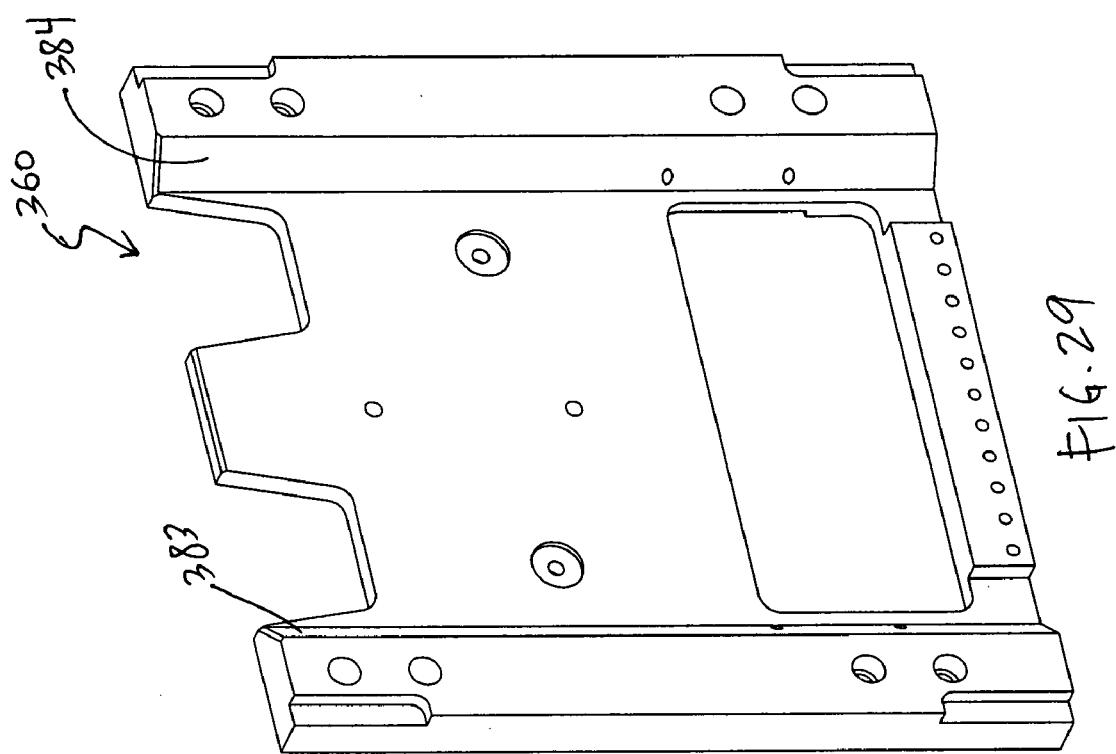
FIG. 29 is a rear view of the front support block of the interface mechanism.
Figure 30:
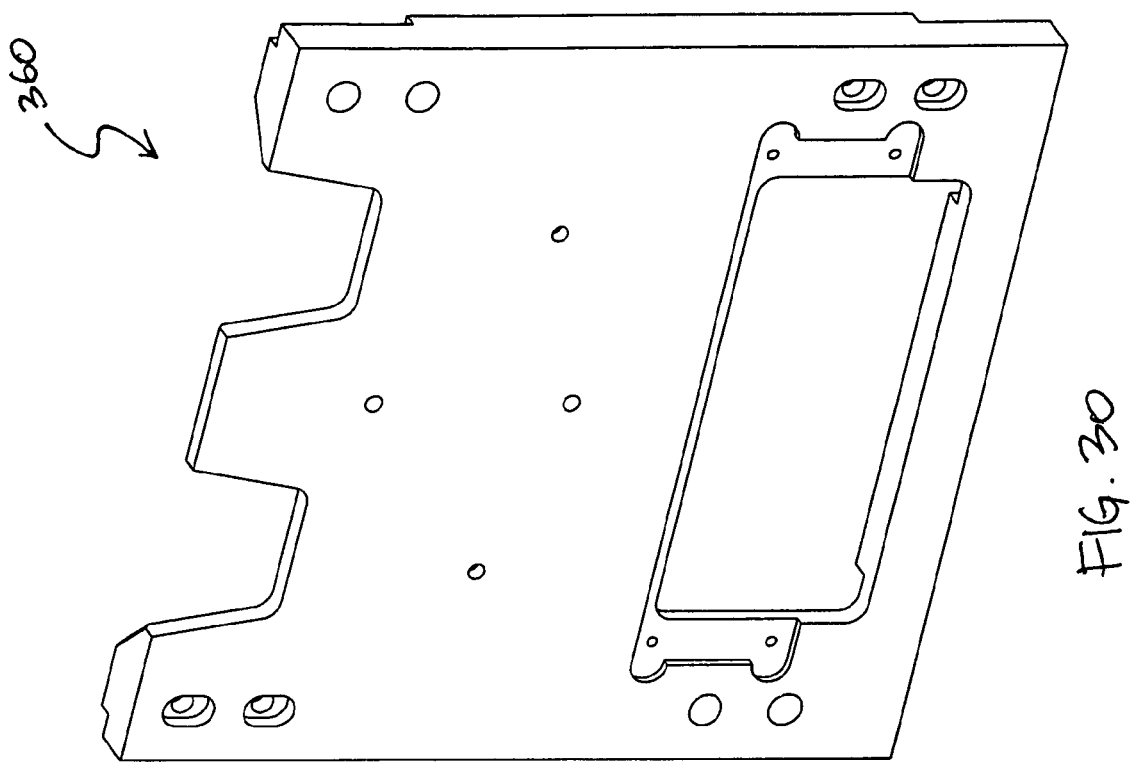
FIG. 30 is a front view of the front support block of the interface mechanism.
Figure 32:
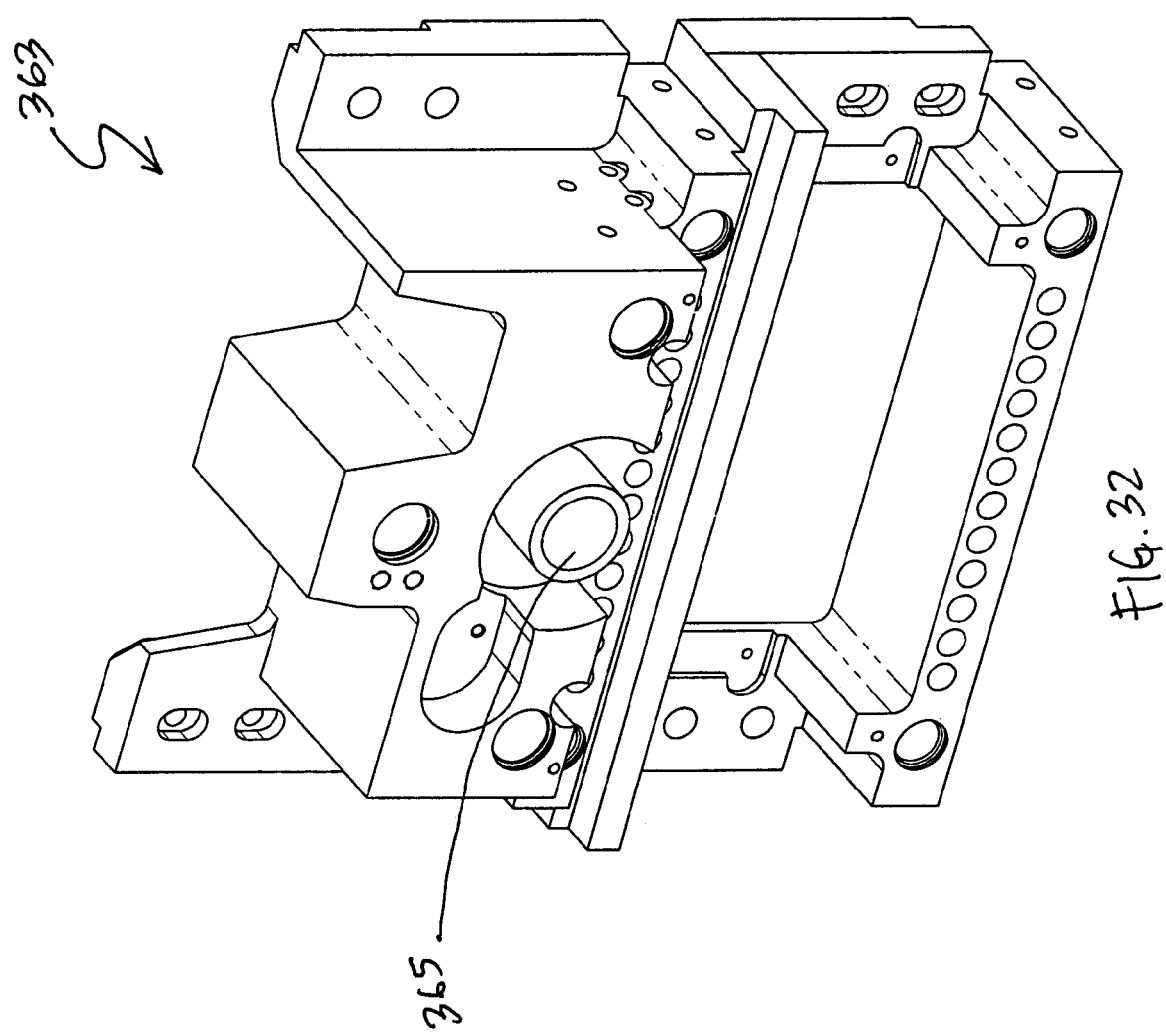
FIG. 32 is a rear view of the rear support block of the interface mechanism.

FIG. 29 is a rear view of the front support block 360 of the interface mechanism 300. FIG. 30 is a front view of the front support block 360 of the interface mechanism 300. FIG. 31 is a front view of the rear support block 363 of the interface mechanism 300. FIG. 32 is a rear view of the rear support block 363 of the interface mechanism 300. Beveled surfaces 381 and 382 are provided on the rear support block 363 and beveled surfaces 383 and 384 are provided on the front support block 364 to receive the beveled edges 391 and 392 (combined in the form of a V-shaped side edge) on either side of the cartridge 100, as best seen from the view in FIGS. 28 and 19A). The assembly of the support blocks 360 and 363 would be evident from the various drawings provided herein.

Operation of Interface Mechanism

With the interface mechanism of the present invention, the operation of the instrument becomes simpler, more reliable, and repeatable. The cartridge with self-contained, pre-aligned optics with respect to the separation channels, can be easily received into the CE system 200 in a positive, secured manner, allowing for improved alignment to external components in the CE system 200, and secure reliable connections of support elements to be made in an automated sequence.

The cartridge 100 is manually placed vertically into the opening at the top of the interface mechanism 300. Optionally, a hinged door or safety latch 350 (shown in 26) that covers the top of the cartridge 100 is provided in the interface mechanism 300. This safety latch is electrically interlocked 61 (FIG. 3) to the interface mechanism 300 by an interlock switch to prevent accidental removal of the cartridge 100, thereby avoiding hazardous conditions. The cartridge 100 comes to rest on the spring-loaded excitation source (LED) barrels 188 in their highest position. If a safety latch is provided, the operator manually closes the door thereby activating the interlock switch. Alternatively, instead of a latch covering the top of the cartridge, an interlocking safety latch is provided in the interface mechanism 300 that latch onto a complementary structure on the cartridge.

After the cartridge has been securely received by the interface mechanism 300, a connection or interfacing sequence is initiated by the BioCalculator (user interface) software from computer 918. In one embodiment, the interfacing sequence is manually initiated by an operator from the operator's control screen (e.g., on the PC 918). An indicia may be displayed in the user interface on the control screen, indicating that the cartridge 100 is securely seated in the interfacing mechanism 300. Alternatively, the interfacing sequence may be initiated automatically in response to a secured reception of the cartridge to the interface mechanism (e.g., by the feedback signal of a sensor).

Upon initiation of the interfacing sequence, the following sequence is executed automatically, in accordance with one embodiment of the present invention. The tips 307 of the locator pins 308 are actuated by the locator barrels 309 to engage the locator seats 310 on the cartridge 100, thereby precisely positioning the cartridge 100 into a final aligned position in relation to the interfacing mechanism 300 for subsequent engagements by the remaining interface barrels. A secondary affect of this positioning is the final seating of the excitation source (LED) barrels 188. The status of the secured engagements of the locator barrels 309 against the locator seats 310 may be displayed on the operator control screen.

The other piston barrels may engage the cartridge 100 together, or in a predetermined sequence. This stage may include the following:

(a) The purge-air piston barrel 303 gets actuated to engage the cartridge reservoir 130.

(b) High voltage anode contact barrels 305 actuate the anode contacts 304 to make engagement with the cartridge anode 134 through the anode contact ports 306.

(c) The emission detection probe piston barrels 320 (schematically shown) actuates the detection probes 170 to make engagements with the conical seat at each capillary.

(d) The cathode contact piston barrels 342 actuates the cathode contacts 340 to make engagement with the cathodes 114 in the cartridge through the cathode contact ports 343.

The interfacing of the support elements to the associated components of the cartridge has been completed. The sequence of the engagement of the various interfaces may differ from the embodiment described above, without departing from the scope and spirit of the present invention. Several of the interfaces may be grouped and actuated together.

A disconnection sequence is provided to disconnect the support elements from the cartridge, allowing the cartridge to be safely removed from the interfacing mechanism 300 in the CE system 200. Disengagement of the cartridge is manually initiated by the operator from the control screen and follows a sequence that is essentially the reverse of the above sequence.

Operation of CE System

Injection of the samples is achieved by electrokinetic methods. The high voltage power supply 76 is used to deliver 0-to-20 KV of electrical field to the gel-filled capillaries for the electrokinetic injection and separations of DNA fragments. Each of the 12-LED's broad band light energy (FWHM=47 nm) is relayed by individual light transmitting optical fibers (multi-mode silica or plastic 200 micron Core fibers, 0.22 N.A.) to each of the capillary's detection zone inside the cartridge 100 for the excitation of the separated DNA fragments.

In operation, the sample handling tray transport mechanism 80, with a 96-well plate (8×12) 70 and 72, is used to introduce the amplified DNA samples (or analytes) to each capillary 140. The X-Z transport mechanism 80 indexes a row of sample carrying wells under the row of capillary tips and dip the tips into the well. By applying a voltage, electrokinetic injection moves a known amount of the DNA sample to the beginning of the separation column 140. After injection, the DNA samples from sample tray 72 may be replaced with a running buffer from tray 70. Alternatively, after injection, the transport mechanism 80 may index to move a row of 12 wells containing buffer solution into position under the cartridge to replace the twelve wells containing DNA samples. By applying high voltage across the total length of the capillary 140, separation of the DNA sample into DNA fragments is achieved. As the fragments approach the end of the capillaries 140 and enter into the detection zone 155, the excitation light energy from each of the twelve LEDs 184 is delivered by the light transmitting optical fibers 116 from outside the detection window, illuminating the migrating DNA fragments from sample tray 72. As the twelve (or twenty-four in the case of dual wavelength detection) LEDs 184 are time-multiplexed (with sampling frequency of 1-100 Hz), twelve emission signals coupled to twelve emission detection fibers 180 will reach the single PMT 178 in a time-staggered manner by a 12-fiber bundle assembly (see U.S. application Ser. No. 10/060,052).

To prepare for the next run with a different sample, the old gel from the previous run is purged from the capillaries by pressuring the reservoir to refill the capillaries with fresh gel. The trays 70 and 72 carries cleaning solutions, waste collection, and samples. The purged gel is collected by one of the trays 70 and 72 by positioning the tips of the capillaries at a row of waste collecting wells in one of the trays. The tips of the capillaries may be cleaned with water or a cleaning solution by positioning and dipping the tips of the capillaries in such solution in the appropriate tray wells. When the capillaries are refilled and ready for the next run, the tips of the capillary are dipped into the samples by repositioning the tray 70 or 72. The above mentioned sequence of process may be programmed as one of the automated functions of the controller 32. The interface mechanism 300 provides the interfacing of support elements in the CE system 200 to the cartridge, such as high voltage, gas pressure, LED radiation source, and detection optics, as described above.

While the invention has been particularly shown and described with reference to the preferred embodiments, it will be understood by those skilled in the art that various changes in form and detail may be made without departing from the spirit, scope, and teaching of the invention. Interface mechanisms including the concept of the present invention may be adapted to receive capillary cartridges of other structural designs. A person skilled in the art will recognize that the instrument incorporating the essence of this invention can also be used for bimolecular analysis other than DNA analysis. For example, by altering the separation gel or buffer, the instrument can also be modified to analyze biomolecules like proteins, carbohydrates, and lipids.

By way of example and not limitation, the detection scheme of the present invention is described in connection with capillary electrophoresis and radiation induced fluorescence detection. It is understood that the present invention is also applicable to detection of analytes separated based on bio-separation phenomenon other than electrophoresis, and detection of radiation emissions other than fluorescence emissions, including other types of emissive radiation, such as phosphorescence, luminescence and chemiluminescence, as well as absorbance based detection.

Furthermore, while the separation channels in the described embodiments are defined by cylindrical columns or tubes, it is understood that the concepts of the present invention is equally applicable to separation channels defined by channels, for example micro-channels (such as square, rectangular or essentially semicircular cross sections) defined by etching in a substrate (micro-fluidics type devices or bio-chips).

The transport mechanism can be configured to move the trays in a horizontal plane, and an additional transport mechanism may be provided to move the cartridge vertically to access the trays.

Accordingly, the disclosed invention is to be considered merely as illustrative and limited in scope only as specified in the appended claims.

We claim:

1. An interface mechanism for interfacing at least an associated component of a capillary cartridge to at least an external component that provides to the associated component of the capillary cartridge a support element required by a bio-analytical process for a bio-sample, comprising:

a support structure supporting the cartridge in relation to the external component, wherein the support structure comprises a location device and an actuator that biases the location device against the capillary cartridge to positively position the capillary cartridge in relation to the external component;

at least one biasing device supported by the support structure, the biasing device supporting and biasing the external component against the associated component of the capillary cartridge, thereby providing the support element to the cartridge to conduct the bio-analytical process; and a controller controlling operation of the biasing device and the location device, wherein the controller is configured to activate the location device to positively position the capillary cartridge prior to activating the biasing device to bias the external component against the associated component of the capillary cartridge.

2. The interface mechanism as in claim 1, wherein the biasing device comprises a compliant member supporting and biasing the external component against the associated component of the capillary cartridge when the capillary cartridge is supported by the support structure.

3. The interface mechanism as in claim 2, wherein the external component provides incident radiation.

4. The interface mechanism as in claim 1, wherein the biasing device comprises an actuator operatively coupled to the external component.

5. The interface mechanism as in claim 4, wherein the actuator comprises at least one of a pneumatic actuator, a electromechanical actuator, and a mechanical actuator.

6. The interface mechanism as in claim 5, further comprising a source of compressed gas operatively coupled to the pneumatic actuator.

7. The interface mechanism as in claim 1, wherein the capillary cartridge is interchangeable and removably supported by the support structure, and wherein the biasing device is structured to removably bias the external component against the associated component of the capillary cartridge to provide a quick connection.

8. The interface mechanism as in claim 1, wherein the external component is associated with a support element comprising at least one of electrical power, a pressurized gas, incident radiation, detection optics.

9. The interface mechanism as in claim 1, wherein the capillary cartridge comprises multiple separation channels, and wherein the support structure supports the capillary cartridge in relation to a plurality of external components, wherein each external component is associated with a support element, and at least one external component being associated with each separation channel.

10. The interface mechanism as in claim 9, wherein the support element associated with each external component comprises at least one of electrical power, a pressurized gas, excitation radiation, detection optics.

11. The interface mechanism as in claim 9, wherein a plurality of external components are associated with each separation channel, the plurality of external components are associated with a plurality of support elements, including at least electrical power, a pressurized gas, incident radiation and detection optics for each separation channel.

12. The interface mechanism as in claim 9, wherein at least one support element is provided by an external component that is separate from other external components associated with similar support element provided to other separation channels.

13. The interface mechanism as in claim 12, wherein the external component provides to the associated component of the capillary cartridge, at least one of incident radiation, detection optics, and electrical power.

14. The interface mechanism as in claim 9, wherein at least one of the plurality of external components is associated with an associated component of the capillary cartridge which is common to the plurality of separation channels.

15. The interface mechanism as in claim 14, wherein said at least one external component provides to the associated component of the capillary cartridge, at least one of a high voltage and a pressurized gas.

16. The interface mechanism as in claim 1, wherein the support structure is provided with a cooling conduit operatively coupled to the capillary cartridge to direct cooling air to the capillary cartridge.

17. A bio-analytical system for conducting a bio-analytical process for a bio-sample in a capillary cartridge, comprising:
   a support for a sample;
   an interface mechanism for interfacing the capillary cartridge to a support element required by the bio-analytical process, comprising:
      at least an external component that provides to the capillary cartridge the support element required by the bio-analytical process;
      a support structure supporting the cartridge in relation to the external component and the sample, wherein the support structure comprises a location device and an actuator that biases the location device against the capillary cartridge to positively position the capillary cartridge in relation to the external component;
      at least one biasing device supported by the support structure, the biasing device supporting and biasing the external component against a designated component of the capillary cartridge, thereby providing the support element to the cartridge to conduct the bio-analytical process; and
   a controller controlling the bio-analytical process in the capillary cartridge, including controlling operation of the interfacing mechanism including controlling operation of the biasing device and the location device, wherein the controller is configured to activate the location device to positively position the capillary cartridge prior to activating the biasing device to bias the external component against the associated component of the capillary cartridge.

18. The bio-analytical system as in claim 17, wherein the interface mechanism comprises all the optics in the system.

* * * * *